(12) United States Patent
Lee et al.

(10) Patent No.: US 8,846,212 B2
(45) Date of Patent: Sep. 30, 2014

(54) ORGANIC METAL COMPLEXES DERIVATIVE AND ORGANIC LIGHT EMITTING DEVICES USING THE SAME

(75) Inventors: Dae-Woong Lee, Daejeon (KR); Jae-Soon Bae, Daejeon (KR); Kong-Kyeom Kim, Daejeon (KR); Jae-Chol Lee, Daejeon (KR); Hyun Nam, Seoul (KR); Seong-So Kim, Paju-si (KR)

(73) Assignee: LG Chem, Ltd., Seoul (KR)

( * ) Notice: Subject to any disclaimer, the term of this patent is extended or adjusted under 35 U.S.C. 154(b) by 841 days.

(21) Appl. No.: 12/452,015

(22) PCT Filed: Jun. 12, 2008

(86) PCT No.: PCT/KR2008/003308
§ 371 (c)(1),
(2), (4) Date: Dec. 11, 2009

(87) PCT Pub. No.: WO2008/153338
PCT Pub. Date: Dec. 18, 2008

(65) Prior Publication Data
US 2010/0117064 A1 May 13, 2010

(30) Foreign Application Priority Data

Jun. 12, 2007 (KR) ........................ 10-2007-0057103

(51) Int. Cl.
| | | |
|---|---|---|
| *C09K 11/06* | (2006.01) | |
| *H01L 51/54* | (2006.01) | |
| *C07F 5/06* | (2006.01) | |
| *H01L 51/00* | (2006.01) | |
| *H01L 51/50* | (2006.01) | |

(52) U.S. Cl.
CPC ......... *C07F 5/069* (2013.01); *C09K 2211/1033* (2013.01); *H01L 51/5016* (2013.01); *H01L 51/0079* (2013.01); *C09K 11/06* (2013.01); *C09K 2211/186* (2013.01); *Y10S 428/917* (2013.01)
USPC ........... 428/690; 428/917; 313/504; 313/506; 257/40; 257/E51.043

(58) Field of Classification Search
CPC .............. C07F 1/02; C07F 3/06; C07F 5/069; C07F 7/006; C07F 11/00; H01L 51/0079; H01L 51/0081; H01L 51/0085; H01L 51/0092; C09K 11/06; C09K 2211/181; C09K 2211/183; C09K 2211/186
See application file for complete search history.

(56) References Cited

U.S. PATENT DOCUMENTS

| | | | |
|---|---|---|---|
| 5,150,006 A | | 9/1992 | Van Slyke et al. |
| 6,001,284 A | * | 12/1999 | Enokida et al. ............... 252/583 |
| 6,805,978 B2 | | 10/2004 | Murase et al. |
| 6,844,087 B1 | | 1/2005 | Andreoni et al. |
| 6,998,492 B2 | | 2/2006 | Seo et al. |
| 7,067,202 B2 | | 6/2006 | Fujii |
| 2002/0037427 A1 | * | 3/2002 | Taguchi ....................... 428/690 |
| 2003/0040627 A1 | | 2/2003 | Fujii |
| 2004/0124769 A1 | | 7/2004 | Ise et al. |

FOREIGN PATENT DOCUMENTS

| | | | |
|---|---|---|---|
| JP | 10-88121 A | | 4/1989 |
| JP | 09-235546 A | | 9/1997 |
| JP | 11-067449 A | | 3/1999 |
| WO | WO 2006/072002 A2 * | | 7/2006 ............ C07F 15/00 |

OTHER PUBLICATIONS

Nikita Sharma et al., "Reactions of (N-phenylsalicylideneiminato)aluminum(III)di(μisopropoxo)di (isopropoxo)aluminium(III) with simple and internally functionalized oximes. Molecular structure of the penta-coordinated complex (2-acetylthiophenyloximato)bis(N-phenylsalicylideneiminato) aluminum(III)", Polyhederon, vol. 22, No. 21, Sep. 1, 2003, pp. 2943-2952, XP55014877.

* cited by examiner

*Primary Examiner* — Michael H Wilson
(74) *Attorney, Agent, or Firm* — McKenna, Long & Aldridge LLP

(57) ABSTRACT

The present invention relates to a novel organic metal complex derivative and to an organic light emitting device comprising the same. The organic metal complex derivative is represented by the following Formula 1:

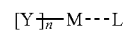

The organic electronic device includes a first electrode, a second electrode, and one or more organic material layers disposed therebetween, and at least one layer of the organic material layers includes the organic metal complex derivative.

8 Claims, 2 Drawing Sheets

ORGANIC METAL COMPLEXES DERIVATIVE AND ORGANIC LIGHT EMITTING DEVICES USING THE SAME

TECHNICAL FIELD

The present invention relates to a novel organic metal complex derivative and an organic light emitting device using the same.

This application is a national phase application of PCT Application No. PCT/KR008/003308, filed on Jun. 12, 2008, which claims priority to Korean Patent Application No. 10-2007-0057103, filed on Jun. 12, 2007. Both PCT/KR2008/003308 and 10-2007-0057103 are hereby incorporated herein by reference for all purposes in their entirety.

BACKGROUND ART

In general, the term "organic light emitting phenomenon" refers to a phenomenon in which electric energy is converted to light energy by means of an organic material. The organic light emitting device using the organic light emitting phenomenon has a structure usually comprising an anode, a cathode and an organic material layer interposed therebetween. Herein, the organic material layer may be mostly formed in a multilayer structure comprising layers of different materials, for example, a hole injecting layer, a hole transporting layer, a light emitting layer, an electron transporting layer, an electron injecting layer and the like, in order to improve efficiency and stability of the organic light emitting device. In the organic light emitting device having such a structure, when a voltage is applied between two electrodes, holes from the anode and electrons from a cathode are injected into the organic material layer, the holes and the electrons injected are combined together to form excitons. Further, when the excitons drop to a ground state, lights are emitted. Such the organic light emitting device is known to have characteristics such as self-luminescence, high brightness, high efficiency, low drive voltage, wide viewing angle, high contrast, and high-speed response.

The materials used for the organic material layer of the organic light emitting device can be classified into a light emitting material and a charge transporting material, for example, a hole injecting material, a hole transporting material, an electron transporting material, and an electron injecting material, according to their functions. The light emitting material can be classified into a high molecular weight type and a low molecular weight type, according to their molecular weight, and divided into a fluorescent material from singlet excited states and a phosphorescent material from triplet excited states according to their light emitting mechanism. Further, the light emitting material can be classified into a blue, green, or red light emitting material and a yellow or orange light emitting material required for giving more natural color, according to a light emitting color.

On the other hand, an efficiency of a device is lowered owing to maximum luminescence wavelength moved to a longer wavelength due to the interaction between the molecules, the deterioration of color purity and the reduction in light emitting efficiency when only one material is used for the light emitting material, and therefore a host/dopant system can be used as the light emitting material for the purpose of enhancing the color purity and the light emitting efficiency through energy transfer. It is based on the principle that if a small amount of a dopant having a smaller energy band gap than a host which forms a light emitting layer, excitons which are generated in the light emitting layer are transported to the dopant, thus emitting a light having a high efficiency. Here, since the wavelength of the host is moved according to the wavelength of the dopant, a light having a desired wavelength can be obtained according the kind of the dopant.

In order to allow the organic light emitting device to fully exhibit the above-mentioned excellent characteristics, a material constituting the organic material layer in the device, for example, a hole injecting material, a hole transporting material, a light emitting material, an electron transporting material, and an electron injecting material should be essentially composed of a stable and efficient material. However, the development of a stable and efficient organic material layer material for the organic light emitting device has not yet been fully realized. Accordingly, the development of new materials is continuously desired. The development of such a material is equally required to the above-mentioned other organic electronic devices.

DISCLOSURE OF INVENTION

Technical Problem

The present inventors have synthesized an organic metal complex derivative having a novel structure, and they found that the derivative exhibits the effect of reducing voltage in an organic light emitting device.

Accordingly, it is an object of the present invention to provide an organic metal complex derivative and an organic light emitting device using the same.

Technical Solution

The present invention provides an organic metal complex derivative represented by the following Formula 1.

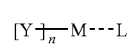

[Formula 1]

wherein Y is a ligand having a unsubstituted or substituted hydroxyaryl-N-hetero ring, and is any one selected from the group consisting of a ligand containing 8-hydroxy-2-methylquinoline, a bidentate Schiff base ligand, and a tetradentate Schiff base ligand, n is 1 to 3, M is a metal having an oxidation number of +2, +3 or +4, L is

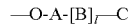

wherein l is 1 to 4,

O is oxygen,

A may be selected from the group consisting of a direct bond; a $C_1$~$C_{40}$ alkylene group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; a $C_3$~$C_{40}$ cycloalkylene group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; a $C_3$~$C_{40}$ heterocycloalkylene group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_6$~$C_{40}$ alkoxy group, a $C_3$~$C_{40}$ cycloalkyl group, a $C_2$~$C_{40}$ heterocycloalkyl group, a $C_6$~$C_{40}$ aryl group, and a $C_5$~$C_{40}$ heteroaryl group; a $C_2$~$C_{40}$ alkenylene group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; a $C_1$~$C_{40}$ alkoxylene group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; an amino group unsubstituted or substituted with one or more groups selected from the group consisting of halogen, deuterium, an amino group, a nitrile group, a nitro group, a $C_1$~$C_{40}$ alkyl group, a $C_1$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; a $C_6$~$C_{40}$ arylene group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; and a $C_5$~$C_{40}$ heteroarylene group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group, or may form an aliphatic, aromatic, heteroaliphatic, or heteroaromatic condensed ring or a spiro bond, together with the adjacent group, B is a compound represented by the following Formula 2,

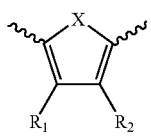

[Formula 2]

wherein X is any one selected from —O—, —NH—, —NR—, —S— and —SiRR'—,

R and R' are bivalent groups, the same as defined in the following $R_1$ and $R_2$, and preferably may be selected from the group consisting of hydrogen; deuterium; a $C_1$~$C_{40}$ alkyl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_3$~$C_{40}$ heteroaryl group; and a $C_6$~$C_{40}$ aryl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group.

$R_1$ and $R_2$ are the same as or different from each other, and the same as defined in the following C, and C may be selected from the group consisting of hydrogen; deuterium; a $C_1$~$C_{40}$ alkyl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; a $C_3$~$C_{40}$ cycloalkyl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; a $C_2$~$C_{40}$ heterocycloalkyl group unsubstituted or substituted with one or more groups selected from the group consisting of halogen, deuterium, an amino group, a nitrile group, a nitro group, a $C_1$~$C_{40}$ alkyl group, a $C_1$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; a $C_2$~$C_{40}$ alkenyl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; a $C_1$~$C_{40}$ alkoxy group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_1$~$C_{40}$ aryl group and a $C_5$~$C_{40}$ heteroaryl group; an amino group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$, cycloalkyl group, a $C_2$~$C_{40}$ heterocycloalkyl group, a $C_6$~$C_{40}$ aryl group and a $C_5$~$C_{40}$ heteroaryl group; a $C_6$~$C_{40}$ aryl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; and a $C_5$~$C_{40}$ heteroaryl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_1$~$C_{40}$ heterocycloalkyl group, a $C_2$~$C_{40}$ aryl group and a $C_5$~$C_{40}$ heteroaryl group, and may form an aliphatic, aromatic, heteroaliphatic, or heteroaromatic condensed ring or a spiro bond, together with the adjacent group.

In addition, the present invention provides an organic electronic device comprising a first electrode, a second electrode, and one or more organic material layers disposed therebetween, wherein at least one layer of the organic material layers comprises the organic metal complex derivative.

In addition, the present invention provides an organic light emitting device having a forward or reverse structure, prepared by sequentially depositing an anode, one or more organic material layers, and a cathode on a substrate, wherein at least one layer of the organic material layers comprises the organic metal complex derivative.

Advantageous Effects

The compound of the present invention is a novel organic metal complex derivative, and can be used for the organic material layer of an organic electronic device and organic light emitting device.

REFERENCE NUMERALS

Figure 1:
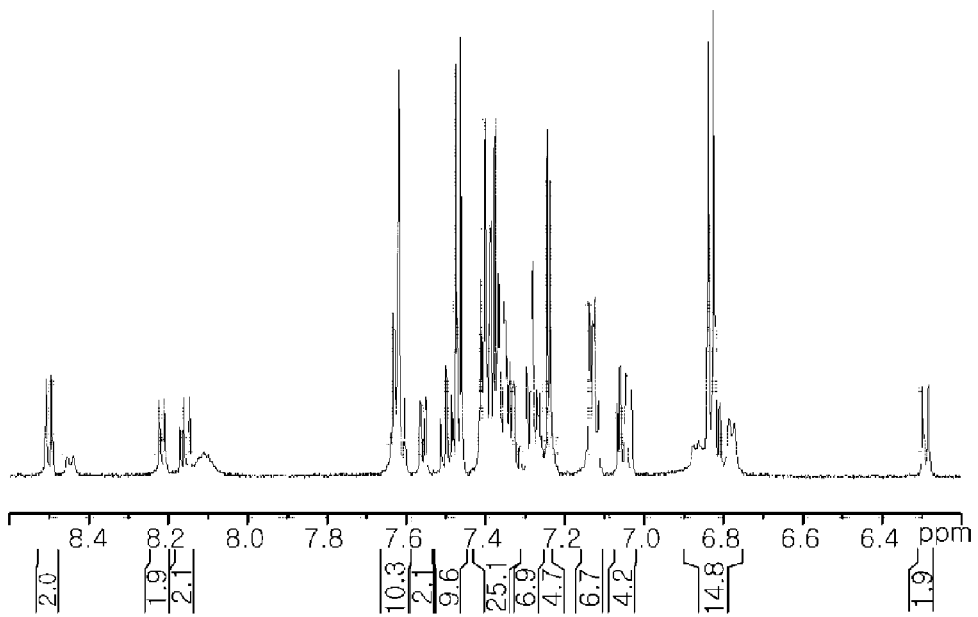
FIG. 1 is a 1H-NMR graph according to Formula 1-38 of the present invention.

1: substrate
2: Anode
3: Hole injecting layer
4: Hole transporting layer
5: Light emitting layer
6: Electron transporting layer
7: Cathode

BEST MODE FOR CARRYING OUT THE INVENTION

Hereinafter, the present invention will be described in more detail.

In Y of Formula 1, the hydroxyaryl-N-hetero ring includes a hetero ring containing at least one nitrogen and an aryl group containing at least one hydroxyl group, in which oxygen of the hydroxyl group and nitrogen of the hetero ring may be coordinately bonded to a metal in the form of pentagon to heptagon.

In addition, with respect to the hydroxyaryl-N-hetero ring, the hetero ring containing at least one nitrogen and the aryl group containing at least one hydroxyl group may be linked by a direct bond, or form an aliphatic, aromatic, heteroaliphatic, or heteroaromatic condensed ring or a spiro bond, together with the adjacent group.

The substituted hydroxyaryl-N-hetero ring may be substituted with one or more selected from the group consisting of hydrogen; deuterium; a $C_1$~$C_{40}$ alkyl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; a $C_3$~$C_{40}$ cycloalkyl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; a $C_2$~$C_{40}$ heterocycloalkyl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; a $C_2$~$C_{40}$ alkenyl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_2$~$C_{40}$ aryl group and a $C_1$~$C_{40}$ heteroaryl group; a $C_1$~$C_{40}$ alkoxy group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; an amino group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; a $C_6$~$C_{40}$ aryl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; and a $C_5$~$C_{40}$ heteroaryl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group, or may form an aliphatic, aromatic, heteroaliphatic, or heteroaromatic condensed ring or a spiro bond, together with the adjacent group.

In Y of Formula 1, the bidentate Schiff base ligand preferably includes a compound represented by the following Formula 3.

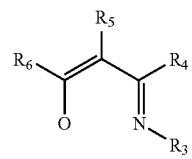

[Formula 3]

wherein $R_3$ to $R_6$ are the same as or different from each other, and may be selected from the group consisting of a $C_1$~$C_{40}$ alkyl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; a $C_3$~$C_{40}$ cycloalkyl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; a $C_2$~$C_{40}$ heterocycloalkyl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; a $C_2$~$C_{40}$ alkenyl group unsubstituted or substituted with one or more groups selected from the group consisting of halogen, deuterium, an amino group, a nitrile group, a nitro group, a $C_1\text{~}C_{40}$ alkyl group, a $C_2\text{~}C_{40}$ alkenyl group, a $C_1\text{~}C_{40}$ alkoxy group, a $C_3\text{~}C_{40}$ cycloalkyl group, a $C_2\text{~}C_{40}$ heterocycloalkyl group, a $C_6\text{~}C_{40}$ aryl group and a $C_5\text{~}C_{40}$ heteroaryl group; a $C_1\text{~}C_{40}$ alkoxy group unsubstituted or substituted with one or more groups selected from the group consisting of halogen, deuterium, an amino group, a nitrile group, a nitro group, a $C_1\text{~}C_{40}$ alkyl group, a $C_2\text{~}C_{40}$ alkenyl group, a $C_1\text{~}C_{40}$ alkoxy group, a $C_3\text{~}C_{40}$ cycloalkyl group, a $C_2\text{~}C_{40}$ heterocycloalkyl group, a $C_6\text{~}C_{40}$ aryl group and a $C_5\text{~}C_{40}$ heteroaryl group; an amino group unsubstituted or substituted with one or more groups selected from the group consisting of halogen, deuterium, an amino group, a nitrile group, a nitro group, a $C_1\text{~}C_{40}$ alkyl group, a $C_2\text{~}C_{40}$ alkenyl group, a $C_1\text{~}C_{40}$ alkoxy group, a $C_3\text{~}C_{40}$ cycloalkyl group, a $C_2\text{~}C_{40}$ heterocycloalkyl group, a $C_6\text{~}C_{40}$ aryl group and a $C_5\text{~}C_{40}$ heteroaryl group; a $C_6\text{~}C_{40}$ aryl group unsubstituted or substituted with one or more groups selected from the group consisting of halogen, deuterium, an amino group, a nitrile group, a nitro group, a $C_1\text{~}C_{40}$ alkyl group, a $C_2\text{~}C_{40}$ alkenyl group, a $C_1\text{~}C_{40}$ alkoxy group, a $C_3\text{~}C_{40}$ cycloalkyl group, a $C_2\text{~}C_{40}$ heterocycloalkyl group, a $C_6\text{~}C_{40}$ aryl group and a $C_5\text{~}C_{40}$ heteroaryl group; and a $C_5\text{~}C_{40}$ heteroaryl group unsubstituted or substituted with one or more groups selected from the group consisting of halogen, deuterium, an amino group, a nitrile group, a nitro group, a $C_1\text{~}C_{40}$ alkyl group, a $C_2\text{~}C_{40}$ alkenyl group, a $C_1\text{~}C_{40}$ alkoxy group, a $C_3\text{~}C_{40}$ cycloalkyl group, a $C_2\text{~}C_{40}$ heterocycloalkyl group, a $C_6\text{~}C_{40}$ aryl group and a $C_5\text{~}C_{40}$ heteroaryl group, or may form an aliphatic, aromatic, heteroaliphatic, or heteroaromatic condensed ring or a spiro bond, together with the adjacent group.

In Y of Formula 1, the tetradentate Schiff base ligand is preferably a compound represented by the following Formula 4.

[Formula 4]

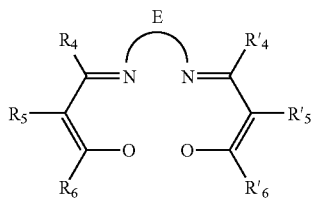

wherein $R_4$ to $R_6$ and $R'_4$ to $R'_6$ are the same as defined in $R_4$ to $R_6$ of Formula 3, E may be selected from the group consisting of a $C_1\text{~}C_{40}$ alkylene group unsubstituted or substituted with one or more groups selected from the group consisting of halogen, deuterium, a nitrile group, a nitro group, a $C_1\text{~}C_{40}$ alkyl group, a $C_2\text{~}C_{40}$ alkenyl group, a $C_1\text{~}C_{40}$ alkoxy group, a $C_3\text{~}C_{40}$ cycloalkyl group, a $C_2\text{~}C_{40}$ heterocycloalkyl group, a $C_6\text{~}C_{40}$ aryl group and a $C_5\text{~}C_{40}$ heteroaryl group; a $C_3\text{~}C_{40}$ cycloalkylene group unsubstituted or substituted with one or more groups selected from the group consisting of halogen, deuterium, a nitrile group, a nitro group, a $C_1\text{~}C_{40}$ alkyl group, a $C_2\text{~}C_{40}$ alkenyl group, a $C_1\text{~}C_{40}$ alkoxy group, a $C_3\text{~}C_{40}$ cycloalkyl group, a $C_2\text{~}C_{40}$ heterocycloalkyl group, a $C_6\text{~}C_{40}$ aryl group and a $C_5\text{~}C_{40}$ heteroaryl group; a $C_2\text{~}C_{40}$ heterocycloalkylene group unsubstituted or substituted with one or more groups selected from the group consisting of halogen, deuterium, a nitrile group, a nitro group, a $C_1\text{~}C_{40}$ alkyl group, a $C_2\text{~}C_{40}$ alkenyl group, a $C_1\text{~}C_{40}$ alkoxy group, a $C_3\text{~}C_{40}$ cycloalkyl group, a $C_2\text{~}C_{40}$ heterocycloalkyl group, a $C_6\text{~}C_{40}$ aryl group, and a $C_5\text{~}C_{40}$ heteroaryl group; a $C_2\text{~}C_{40}$ alkenylene group unsubstituted or substituted with one or more groups selected from the group consisting of halogen, deuterium, a nitrile group, a nitro group, a $C_1\text{~}C_{40}$ alkyl group, a $C_2\text{~}C_{40}$ alkenyl group, a $C_1\text{~}C_{40}$ alkoxy group, a $C_3\text{~}C_{40}$ cycloalkyl group, a $C_2\text{~}C_{40}$ heterocycloalkyl group, a $C_6\text{~}C_{40}$ aryl group and a $C_5\text{~}C_{40}$ heteroaryl group; a $C_6\text{~}C_{40}$ arylene group unsubstituted or substituted with one or more groups selected from the group consisting of halogen, deuterium, a nitrile group, a nitro group, a $C_1\text{~}C_{40}$ alkyl group, a $C_2\text{~}C_{40}$ alkenyl group, a $C_1\text{~}C_{40}$ alkoxy group, a $C_3\text{~}C_{40}$ cycloalkyl group, a $C_2\text{~}C_{40}$ heterocycloalkyl group, a $C_6\text{~}C_{40}$ aryl group and a $C_5\text{~}C_{40}$ heteroaryl group; and a $C_5\text{~}C_{40}$ heteroarylene group unsubstituted or substituted with one or more groups selected from the group consisting of halogen, deuterium, a nitrile group, a nitro group, a $C_1\text{~}C_{40}$ alkyl group, a $C_2\text{~}C_{40}$ alkenyl group, a $C_1\text{~}C_{40}$ alkoxy group, a $C_3\text{~}C_{40}$ cycloalkyl group, a $C_2\text{~}C_{40}$ heterocycloalkyl group, a $C_6\text{~}C_{40}$ aryl group and a $C_5\text{~}C_{40}$ heteroaryl group, or may form an aliphatic, aromatic, heteroaliphatic, or heteroaromatic condensed ring or a spiro bond, together with the adjacent group.

In Formula 1, M is a metal having an oxidation number of 2 to 4, and may preferably include aluminum, zinc, zirconium, iridium, gallium, molybdenum or the like.

The organic metal complex derivative represented by Formula 1 according to the present invention is preferably a compound represented by $[Y]_2\text{-M-O-A-}[B]_j\text{—C}$, wherein M is aluminum; A is a $C_6\text{~}C_{40}$ aryl group unsubstituted or substituted with one or more groups selected from the group consisting of halogen, deuterium, a nitrile group, a nitro group, a $C_1\text{~}C_{40}$ alkyl group, a $C_2\text{~}C_{40}$ alkenyl group, a $C_1\text{~}C_{40}$ alkoxy group, a $C_3\text{~}C_{40}$ cycloalkyl group, a $C_2\text{~}C_{40}$ heterocycloalkyl group, a $C_6\text{~}C_{40}$ aryl group and a $C_5\text{~}C_{40}$ heteroaryl group; B is a compound represented by Formula 2, wherein X is —S—; C is a $C_6\text{~}C_{40}$ aryl group unsubstituted or substituted with one or more groups selected from the group consisting of halogen, deuterium, a nitrile group, a nitro group, a $C_1\text{~}C_{40}$ alkyl group, a $C_2\text{~}C_{40}$ alkenyl group, a $C_1\text{~}C_{40}$ alkoxy group, a $C_3\text{~}C_{40}$ cycloalkyl group, a $C_2\text{~}C_{40}$ heterocycloalkyl group, a $C_6\text{~}C_{40}$ aryl group and a $C_5\text{~}C_{40}$ heteroaryl group.

In particular, the organic metal complex derivative represented by Formula 1 according to the present invention is selected from the group consisting of the following Formulae 1-1 to 1-210. In this connection, Y is a hydroxyaryl-N-hetero ring.

Table 1

TABLE 1

| Formula | M | A | B | l | C |
|---|---|---|---|---|---|
| 1-1 | Al | direct bond | 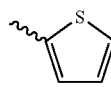 | 1 | H |

TABLE 1-continued
| Formula | M | A | B | l | C |
|---|---|---|---|---|---|
| 1-2 | Al | direct bond | 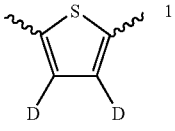 | 1 | D |
| 1-3 | Al | direct bond | 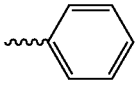 | 1 | 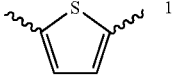 |
| 1-4 | Al | direct bond | 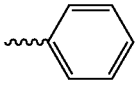 | 1 | 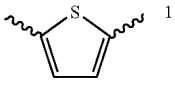 |
| 1-5 | Al | direct bond | 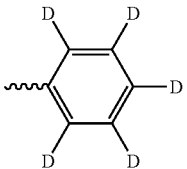 | 1 | 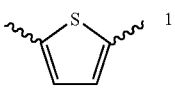 |
| 1-6 | Al | direct bond | 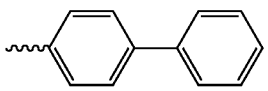 | 1 | 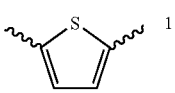 |
| 1-7 | Al | direct bond | 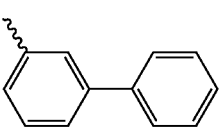 | 1 | 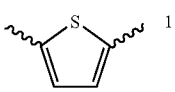 |
| 1-8 | Al | direct bond | 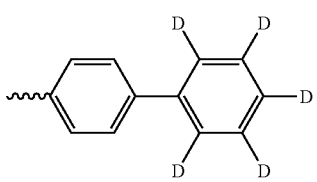 | 1 | 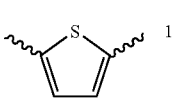 |
| 1-9 | Al | direct bond | 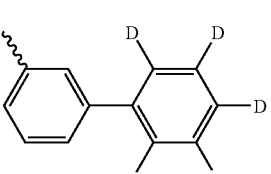 | 1 | 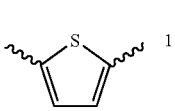 |
| 1-10 | Al | direct bond | 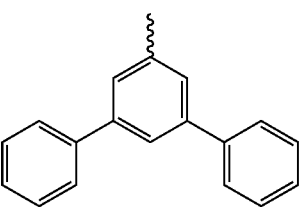 | 1 | 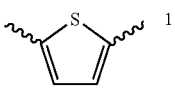 |
| 1-11 | Al | direct bond | 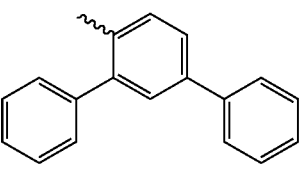 | 1 | 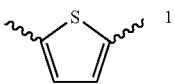 |

TABLE 1-continued
| Formula | M | A | B | l | C |
|---|---|---|---|---|---|
| 1-12 | Al | direct bond | 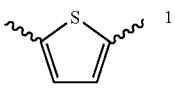 | 1 | 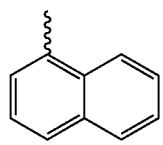 |
| 1-13 | Al | direct bond | 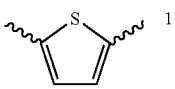 | 1 | 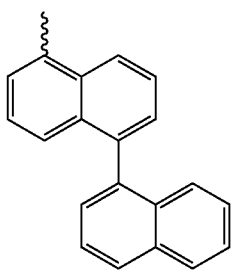 |
| 1-14 | Al | direct bond | 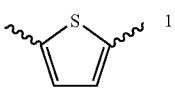 | 1 | 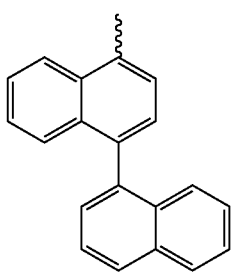 |
| 1-15 | Al | direct bond | 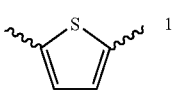 | 1 | 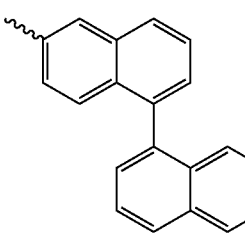 |
| 1-16 | Al | direct bond | 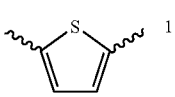 | 1 | 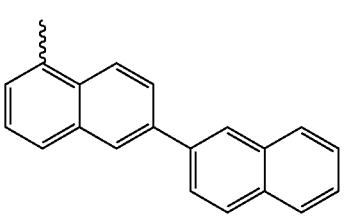 |
| 1-17 | Al | direct bond | 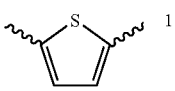 | 1 | 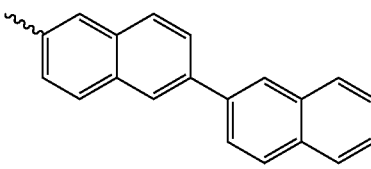 |
| 1-18 | Al | direct bond | 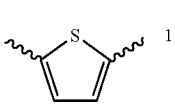 | 1 | 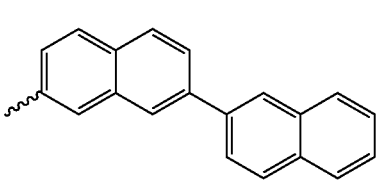 |

TABLE 1-continued
| Formula | M | A | B | l | C |
|---|---|---|---|---|---|
| 1-19 | Al | direct bond | 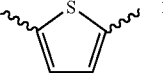 | 1 | 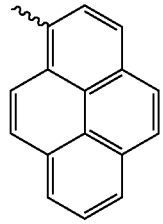 |
| 1-20 | Al | direct bond | 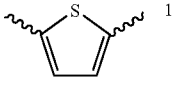 | 1 | 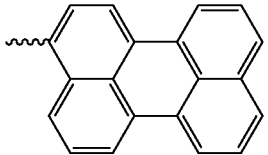 |
| 1-21 | Al | direct bond | 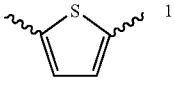 | 1 | 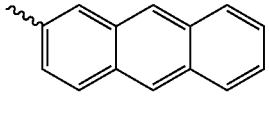 |
| 1-22 | Al | direct bond | 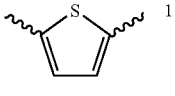 | 1 | 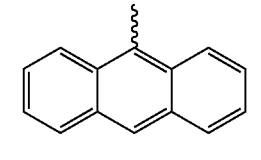 |
| 1-23 | Al | direct bond |  | 1 | 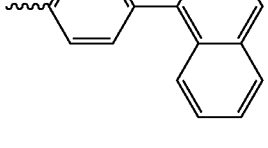 |
| 1-24 | Al | direct bond | 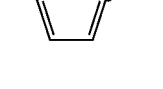 | 1 | 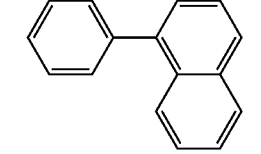 |
| 1-25 | Al | direct bond |  | 1 | 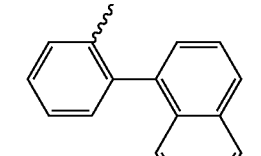 |
| 1-26 | Al | direct bond | 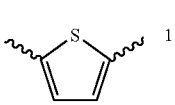 | 1 | 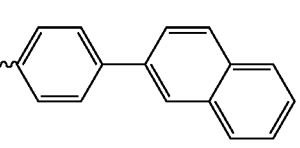 |
| 1-27 | Al | direct bond | 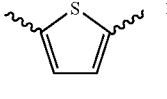 | 1 | 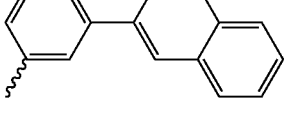 |

TABLE 1-continued
| Formula | M | A | B | l | C |
|---|---|---|---|---|---|
| 1-28 | Al | direct bond | 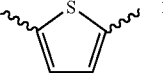 | 1 | 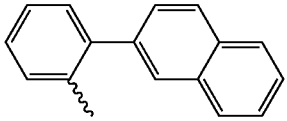 |
| 1-29 | Al | direct bond | 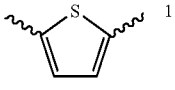 | 1 | 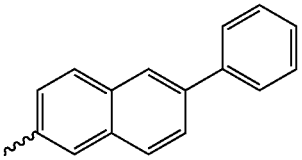 |
| 1-30 | Al | direct bond | 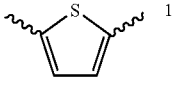 | 1 | 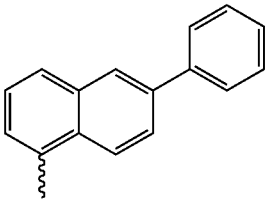 |
| 1-31 | Al | direct bond | 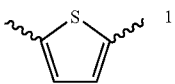 | 1 | 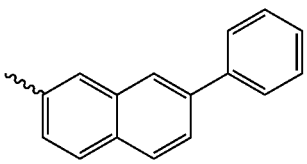 |
| 1-32 | Al | direct bond | 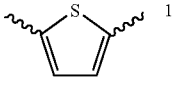 | 1 | 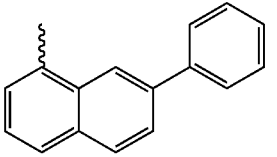 |
| 1-33 | Al | direct bond | 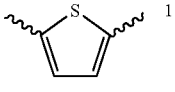 | 1 | 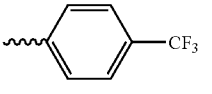 |
| 1-34 | Al | direct bond |  | 1 | 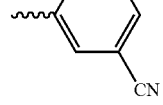 |
| 1-35 | Al | direct bond | 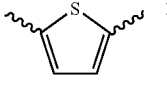 | 1 | 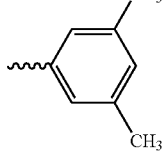 |
| 1-36 | Al |  | 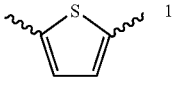 | 1 | H |
| 1-37 | Al | 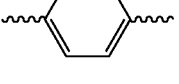 | 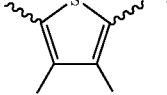 | 1 | D |

TABLE 1-continued
| Formula | M | A | B | l | C |
|---|---|---|---|---|---|
| 1-38 | Al | 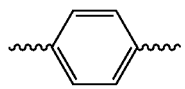 | 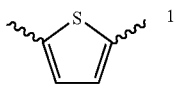 | 1 | 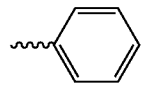 |
| 1-39 | Al | 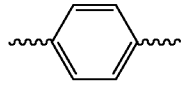 | 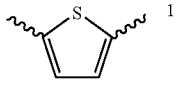 | 1 | 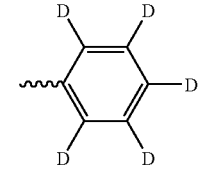 |
| 1-40 | Al | 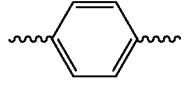 | 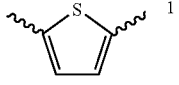 | 1 | 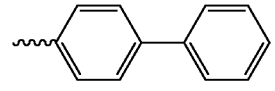 |
| 1-41 | Al | 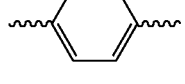 |  | 1 | 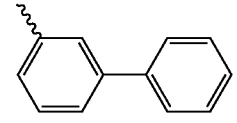 |
| 1-42 | Al | 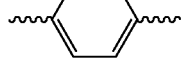 | 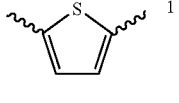 | 1 | 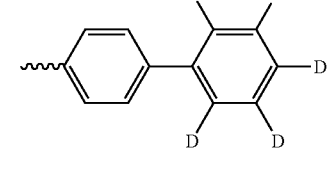 |
| 1-43 | Al | 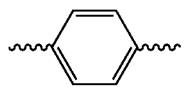 | 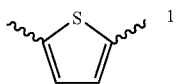 | 1 | 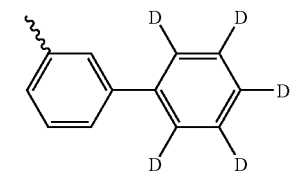 |
| 1-44 | Al | 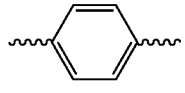 | 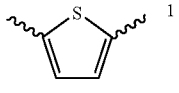 | 1 | 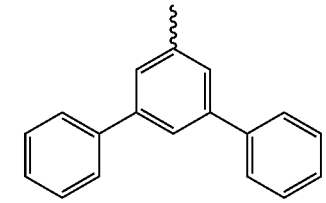 |
| 1-45 | Al | 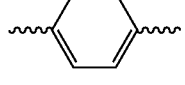 |  | 1 | 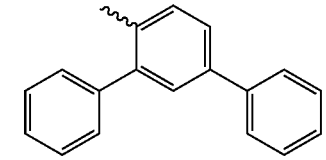 |
| 1-46 | Al | 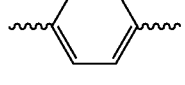 |  | 1 | 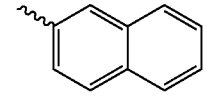 |
| 1-47 | Al | 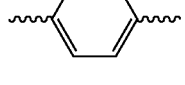 |  | 1 | 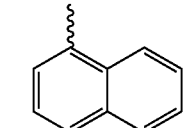 |

TABLE 1-continued

| Formula | M | A | B | l | C |
|---|---|---|---|---|---|
| 1-48 | Al | phenylene | thiophene | 1 | 1,1'-binaphthyl (1,1-linked) |
| 1-49 | Al | phenylene | thiophene | 1 | 1,1'-binaphthyl |
| 1-50 | Al | phenylene | thiophene | 1 | 1,1'-binaphthyl |
| 1-51 | Al | phenylene | thiophene | 1 | 2,2'-binaphthyl |
| 1-52 | Al | phenylene | thiophene | 1 | 2,2'-binaphthyl |
| 1-53 | Al | phenylene | thiophene | 1 | 2,2'-binaphthyl |
| 1-54 | Al | phenylene | thiophene | 1 | pyrenyl |

TABLE 1-continued

| Formula | M | A | B | l | C |
|---|---|---|---|---|---|
| 1-55 | Al | phenylene | thiophene | 1 | perylenyl |
| 1-56 | Al | phenylene | thiophene | 1 | anthracen-2-yl |
| 1-57 | Al | phenylene | thiophene | 1 | anthracen-9-yl |
| 1-58 | Al | phenylene | thiophene | 1 | 4-(naphthalen-1-yl)phenyl |
| 1-59 | Al | phenylene | thiophene | 1 | 3-(naphthalen-1-yl)phenyl |
| 1-60 | Al | phenylene | thiophene | 1 | 2-(naphthalen-1-yl)phenyl |
| 1-61 | Al | phenylene | thiophene | 1 | 4-(naphthalen-2-yl)phenyl |
| 1-62 | Al | phenylene | thiophene | 1 | 3-(naphthalen-2-yl)phenyl |
| 1-63 | Al | phenylene | thiophene | 1 | 2-(naphthalen-2-yl)phenyl |
| 1-64 | Al | phenylene | thiophene | 1 | 6-phenylnaphthalen-2-yl |

TABLE 1-continued

| Formula | M | A | B | l | C |
|---|---|---|---|---|---|
| 1-65 | Al | *para*-phenylene | thiophene-2,5-diyl | 1 | 5-phenyl-naphthalen-1-yl (phenyl at 2-position of naphthalene, attached at 5-position) |
| 1-66 | Al | *para*-phenylene | thiophene-2,5-diyl | 1 | 6-phenyl-naphthalen-2-yl |
| 1-67 | Al | *para*-phenylene | thiophene-2,5-diyl | 1 | 6-phenyl-naphthalen-1-yl |
| 1-68 | Al | *para*-phenylene | thiophene-2,5-diyl | 1 | 4-(trifluoromethyl)phenyl |
| 1-69 | Al | *para*-phenylene | thiophene-2,5-diyl | 1 | 3-cyanophenyl |
| 1-70 | Al | *para*-phenylene | thiophene-2,5-diyl | 1 | 3,5-dimethylphenyl |
| 1-71 | Al | *meta*-phenylene | thiophene-2,5-diyl | 1 | H |
| 1-72 | Al | *meta*-phenylene | thiophene-2,5-diyl (3,4-D₂) | 1 | D |
| 1-73 | Al | *meta*-phenylene | thiophene-2,5-diyl | 1 | phenyl |
| 1-74 | Al | *meta*-phenylene | thiophene-2,5-diyl | 1 | phenyl-d₅ |

TABLE 1-continued
| Formula | M | A | B | l | C |
|---|---|---|---|---|---|
| 1-75 | Al | 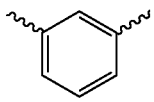 |  | 1 | 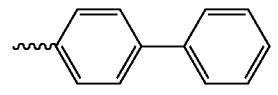 |
| 1-76 | Al | 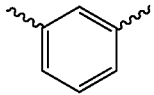 | 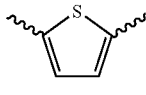 | 1 | 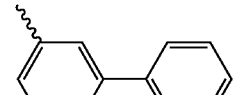 |
| 1-77 | Al | 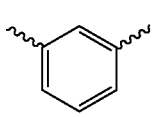 |  | 1 | 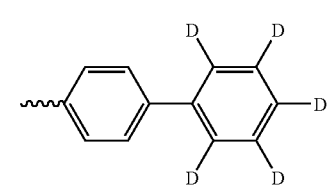 |
| 1-78 | Al | 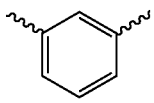 |  | 1 | 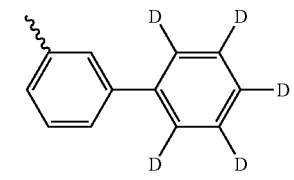 |
| 1-79 | Al | 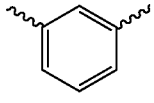 |  | 1 | 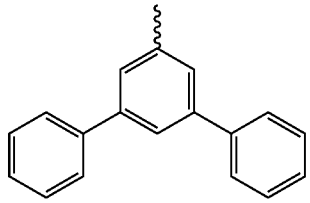 |
| 1-80 | Al | 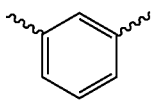 |  | 1 | 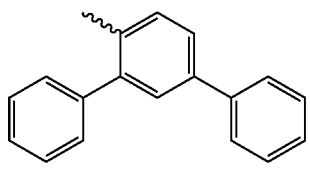 |
| 1-81 | Al | 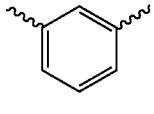 |  | 1 | 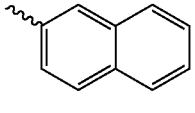 |
| 1-82 | Al | 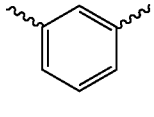 |  | 1 | 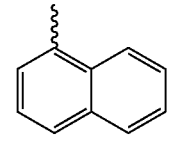 |
| 1-83 | Al | 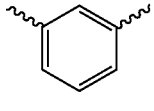 |  | 1 | 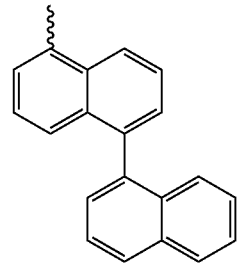 |

TABLE 1-continued
| Formula | M | A | B | l | C |
|---|---|---|---|---|---|
| 1-84 | Al | 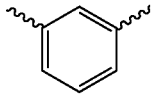 | 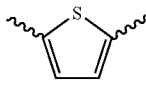 | 1 | 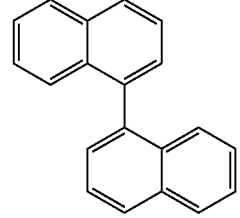 |
| 1-85 | Al | 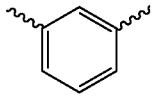 | 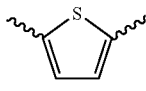 | 1 | 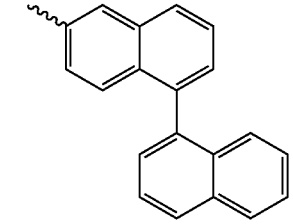 |
| 1-86 | Al | 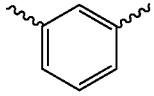 | 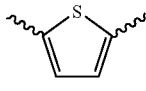 | 1 | 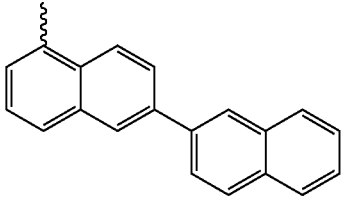 |
| 1-87 | Al | 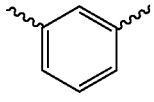 |  | 1 | 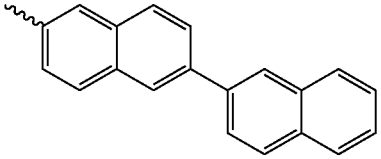 |
| 1-88 | Al | 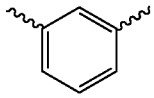 | 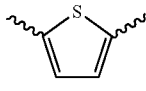 | 1 | 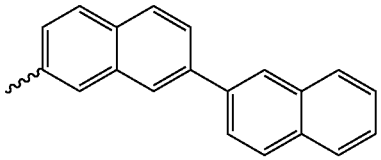 |
| 1-89 | Al | 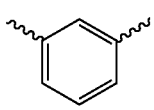 |  | 1 | 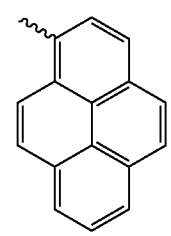 |
| 1-90 | Al |  | 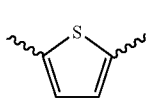 | 1 | 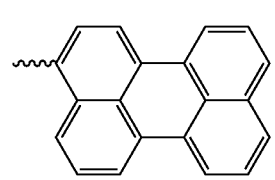 |
| 1-91 | Al | 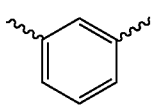 |  | 1 | 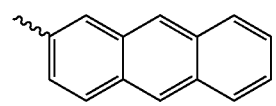 |

TABLE 1-continued

| Formula | M | A | B | l | C |
|---|---|---|---|---|---|
| 1-92 | Al | phenylene | thiophene | 1 | anthracen-9-yl |
| 1-93 | Al | phenylene | thiophene | 1 | 4-(naphthalen-1-yl)phenyl |
| 1-94 | Al | phenylene | thiophene | 1 | 3-(naphthalen-1-yl)phenyl |
| 1-95 | Al | phenylene | thiophene | 1 | 2-(naphthalen-1-yl)phenyl |
| 1-96 | Al | phenylene | thiophene | 1 | 4-(naphthalen-2-yl)phenyl |
| 1-97 | Al | phenylene | thiophene | 1 | 3-(naphthalen-2-yl)phenyl |
| 1-98 | Al | phenylene | thiophene | 1 | 2-(naphthalen-2-yl)phenyl |
| 1-99 | Al | phenylene | thiophene | 1 | 6-phenylnaphthalen-2-yl |
| 1-100 | Al | phenylene | thiophene | 1 | 5-phenylnaphthalen-2-yl |

TABLE 1-continued

| Formula | M | A | B | l | C |
|---|---|---|---|---|---|
| 1-101 | Al | phenylene (1,3) | thiophene (2,5) | 1 | 6-phenylnaphthalen-2-yl |
| 1-102 | Al | phenylene (1,3) | thiophene (2,5) | 1 | 7-phenylnaphthalen-1-yl |
| 1-103 | Al | phenylene (1,3) | thiophene (2,5) | 1 | 4-(trifluoromethyl)phenyl |
| 1-104 | Al | phenylene (1,3) | thiophene (2,5) | 1 | 3-cyanophenyl |
| 1-105 | Al | phenylene (1,3) | thiophene (2,5) | 1 | 3,5-dimethylphenyl |
| 1-106 | Al | 4,4'-biphenylene | thiophene (2,5) | 1 | H |
| 1-107 | Al | 4,4'-biphenylene | thiophene (2,5) | 1 | D |
| 1-108 | Al | 4,4'-biphenylene | thiophene (2,5) | 1 | phenyl |
| 1-109 | Al | 4,4'-biphenylene | thiophene (2,5) | 1 | phenyl-d5 |
| 1-110 | Al | 4,4'-biphenylene | thiophene (2,5) | 1 | 4-biphenylyl |
| 1-111 | Al | 4,4'-biphenylene | thiophene (2,5) | 1 | 3-biphenylyl |

TABLE 1-continued

| Formula | M | A | B | l | C |
|---|---|---|---|---|---|
| 1-112 | Al | biphenyl-4,4'-diyl | thiophene-2,5-diyl | 1 | 4-(perdeuterophenyl)phenyl |
| 1-113 | Al | biphenyl-4,4'-diyl | thiophene-2,5-diyl | 1 | 3-(perdeuterophenyl)phenyl |
| 1-114 | Al | biphenyl-4,4'-diyl | thiophene-2,5-diyl | 1 | 3,5-diphenylphenyl |
| 1-115 | Al | biphenyl-4,4'-diyl | thiophene-2,5-diyl | 1 | 2,3-diphenylphenyl |
| 1-116 | Al | biphenyl-4,4'-diyl | thiophene-2,5-diyl | 1 | naphthalen-2-yl |
| 1-117 | Al | biphenyl-4,4'-diyl | thiophene-2,5-diyl | 1 | naphthalen-1-yl |
| 1-118 | Al | biphenyl-4,4'-diyl | thiophene-2,5-diyl | 1 | 1,1'-binaphthalen-4-yl |
| 1-119 | Al | biphenyl-4,4'-diyl | thiophene-2,5-diyl | 1 | 1,1'-binaphthalen-4-yl |

TABLE 1-continued
| Formula | M | A | B | l | C |
|---|---|---|---|---|---|
| 1-120 | Al | 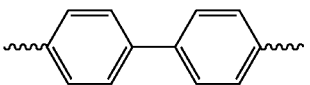 | 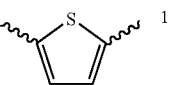 | 1 | 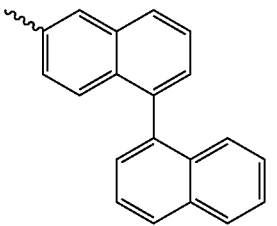 |
| 1-121 | Al | 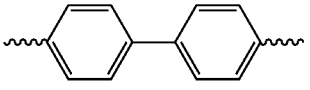 | 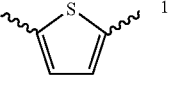 | 1 | 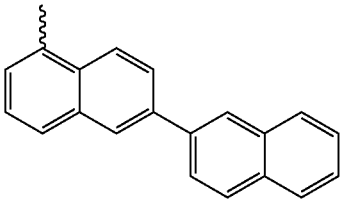 |
| 1-122 | Al | 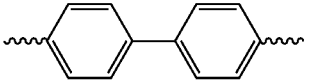 | 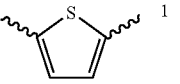 | 1 | 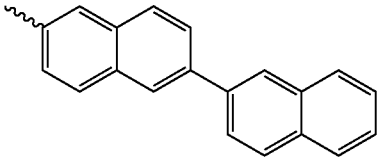 |
| 1-123 | Al | 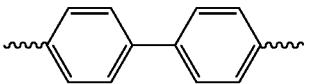 | 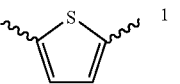 | 1 | 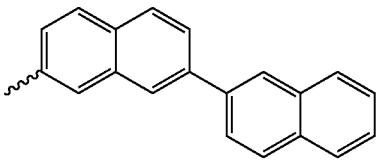 |
| 1-124 | Al | 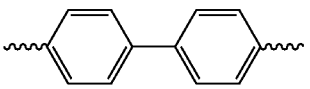 | 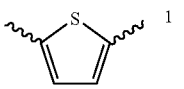 | 1 | 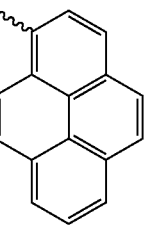 |
| 1-125 | Al | 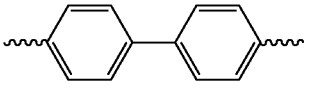 | 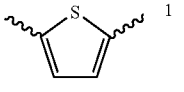 | 1 | 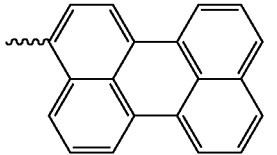 |
| 1-126 | Al | 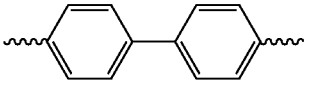 | 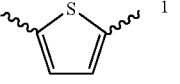 | 1 | 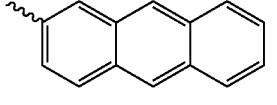 |
| 1-127 | Al | 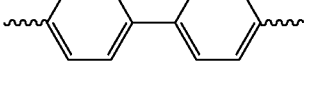 |  | 1 | 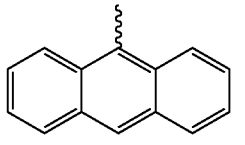 |

TABLE 1-continued
| Formula | M | A | B | l | C |
|---|---|---|---|---|---|
| 1-128 | Al | 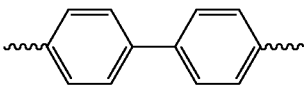 | 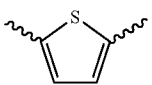 | 1 | 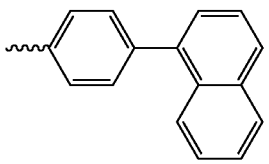 |
| 1-129 | Al | 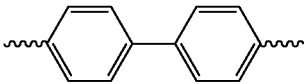 | 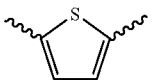 | 1 | 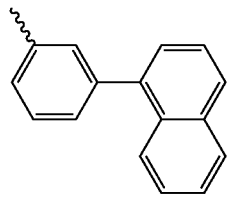 |
| 1-130 | Al | 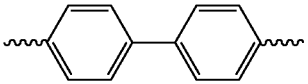 | 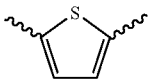 | 1 | 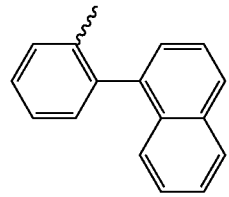 |
| 1-131 | Al | 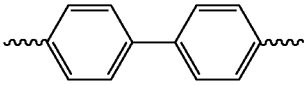 | 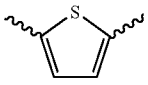 | 1 | 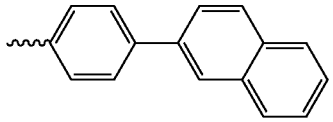 |
| 1-132 | Al | 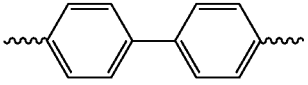 | 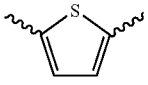 | 1 | 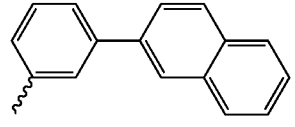 |
| 1-133 | Al | 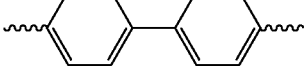 | 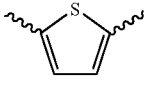 | 1 | 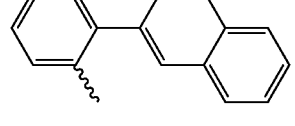 |
| 1-134 | Al | 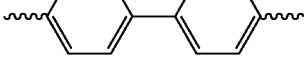 |  | 1 | 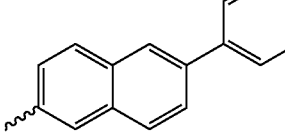 |
| 1-135 | Al | 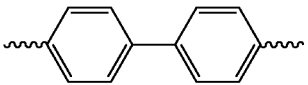 | 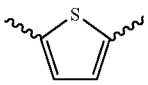 | 1 | 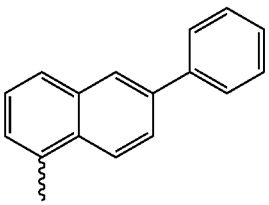 |
| 1-136 | Al | 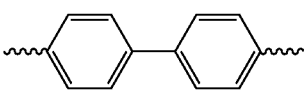 | 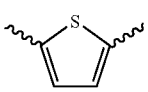 | 1 | 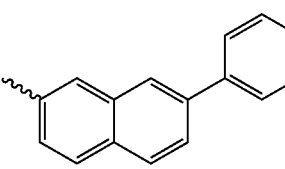 |

TABLE 1-continued
| Formula | M | A | B | l | C |
|---|---|---|---|---|---|
| 1-137 | Al | 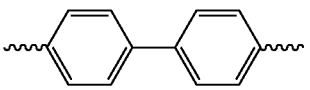 | 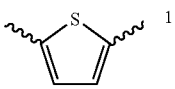 | 1 | 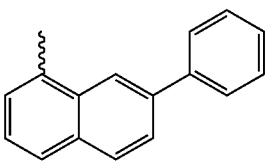 |
| 1-138 | Al | 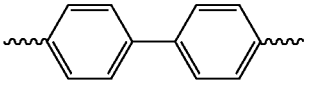 | 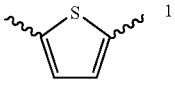 | 1 | 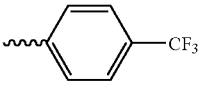 |
| 1-139 | Al | 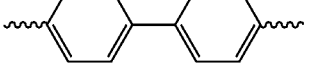 |  | 1 | 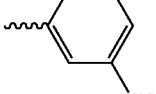 |
| 1-140 | Al | 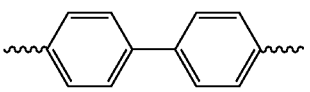 | 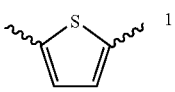 | 1 | 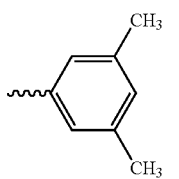 |
| 1-141 | Al | 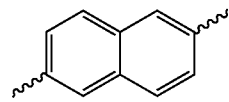 | 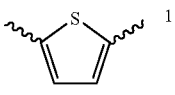 | 1 | H |
| 1-142 | Al | 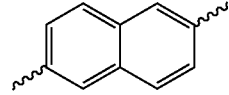 | 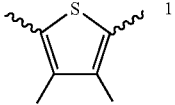 | 1 | D |
| 1-143 | Al | 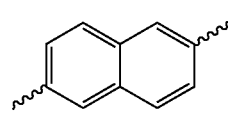 | 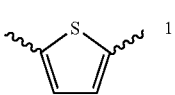 | 1 | 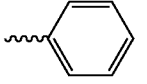 |
| 1-144 | Al | 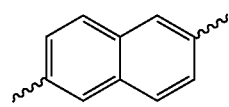 | 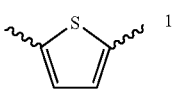 | 1 | 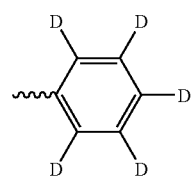 |
| 1-145 | Al | 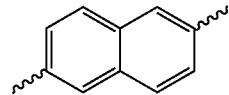 | 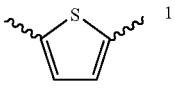 | 1 | 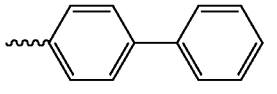 |
| 1-146 | Al | 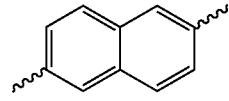 | 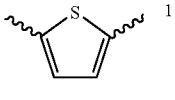 | 1 | 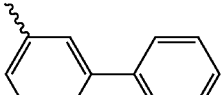 |
| 1-147 | Al | 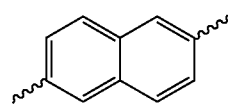 | 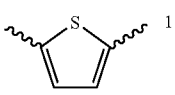 | 1 | 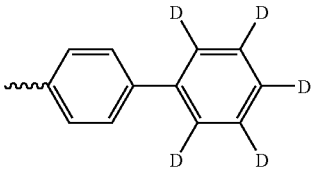 |

TABLE 1-continued
| Formula | M | A | B | l | C |
|---|---|---|---|---|---|
| 1-148 | Al | 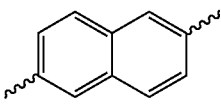 | 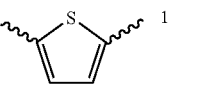 | 1 | 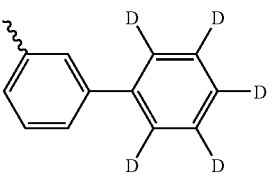 |
| 1-149 | Al | 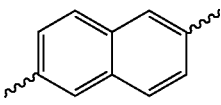 | 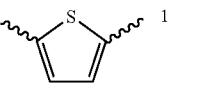 | 1 | 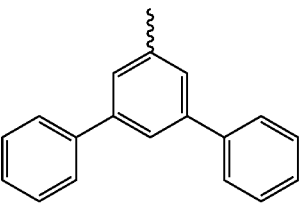 |
| 1-150 | Al | 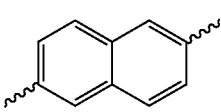 | 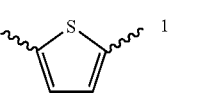 | 1 | 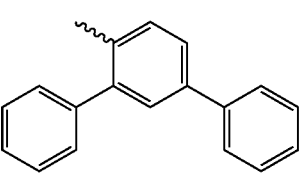 |
| 1-151 | Al | 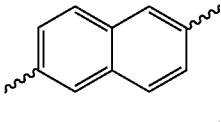 | 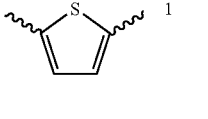 | 1 | 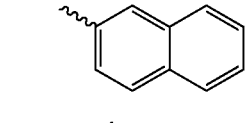 |
| 1-152 | Al | 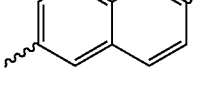 |  | 1 | 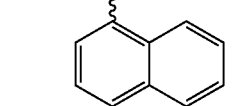 |
| 1-153 | Al | 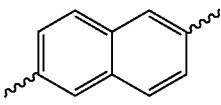 | 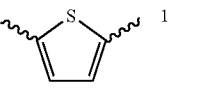 | 1 | 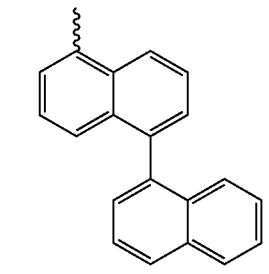 |
| 1-154 | Al | 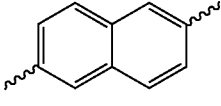 | 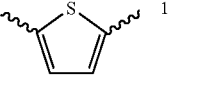 | 1 | 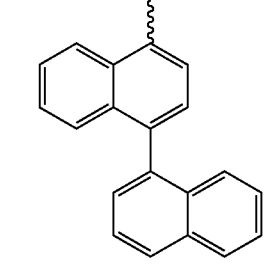 |
| 1-155 | Al | 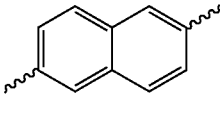 | 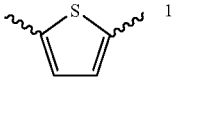 | 1 | 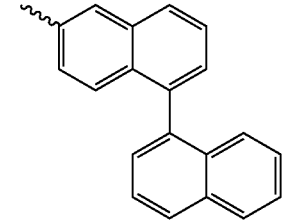 |

TABLE 1-continued
| Formula | M | A | B | l | C |
|---|---|---|---|---|---|
| 1-156 | Al |  |  | 1 |  |
| 1-157 | Al |  |  | 1 |  |
| 1-158 | Al |  |  | 1 |  |
| 1-159 | Al |  |  | 1 |  |
| 1-160 | Al |  |  | 1 |  |
| 1-161 | Al |  |  | 1 |  |
| 1-162 | Al |  |  | 1 |  |
| 1-163 | Al |  |  | 1 |  |

TABLE 1-continued

| Formula | M | A | B | l | C |
|---|---|---|---|---|---|
| 1-164 | Al | naphthalene-2,6-diyl | thiophene-2,5-diyl | 1 | 3-(naphthalen-1-yl)phenyl |
| 1-165 | Al | naphthalene-2,6-diyl | thiophene-2,5-diyl | 1 | 2-(naphthalen-1-yl)phenyl |
| 1-166 | Al | naphthalene-2,6-diyl | thiophene-2,5-diyl | 1 | 4-(naphthalen-2-yl)phenyl |
| 1-167 | Al | naphthalene-2,6-diyl | thiophene-2,5-diyl | 1 | 3-(naphthalen-2-yl)phenyl |
| 1-168 | Al | naphthalene-2,6-diyl | thiophene-2,5-diyl | 1 | 2-(naphthalen-2-yl)phenyl |
| 1-169 | Al | naphthalene-2,6-diyl | thiophene-2,5-diyl | 1 | 6-phenylnaphthalen-2-yl |
| 1-170 | Al | naphthalene-2,6-diyl | thiophene-2,5-diyl | 1 | 5-phenylnaphthalen-1-yl (substituted naphthyl) |
| 1-171 | Al | naphthalene-2,6-diyl | thiophene-2,5-diyl | 1 | 7-phenylnaphthalen-2-yl |
| 1-172 | Al | naphthalene-2,6-diyl | thiophene-2,5-diyl | 1 | 7-phenylnaphthalen-1-yl |

TABLE 1-continued

| Formula | M | A | B | l | C |
|---|---|---|---|---|---|
| 1-173 | Al | 2,6-naphthalene | thiophene-2,5-diyl | 1 | 4-(CF₃)phenyl |
| 1-174 | Al | 2,6-naphthalene | thiophene-2,5-diyl | 1 | 3-(CN)phenyl |
| 1-175 | Al | 2,6-naphthalene | thiophene-2,5-diyl | 1 | 3,5-dimethylphenyl |
| 1-176 | Al | 4-phenyl-2,6-naphthalene | thiophene-2,5-diyl | 1 | H |
| 1-177 | Al | 4-phenyl-2,6-naphthalene | 3,4-dideutero-thiophene-2,5-diyl | 1 | D |
| 1-178 | Al | 4-phenyl-2,6-naphthalene | thiophene-2,5-diyl | 1 | phenyl |
| 1-179 | Al | 4-phenyl-2,6-naphthalene | thiophene-2,5-diyl | 1 | pentadeuterophenyl |
| 1-180 | Al | 4-phenyl-2,6-naphthalene | thiophene-2,5-diyl | 1 | 4-biphenyl |
| 1-181 | Al | 4-phenyl-2,6-naphthalene | thiophene-2,5-diyl | 1 | 3-biphenyl |
| 1-182 | Al | 4-phenyl-2,6-naphthalene | thiophene-2,5-diyl | 1 | 4-(pentadeuterophenyl)phenyl |

TABLE 1-continued

| Formula | M | A | B | l | C |
|---|---|---|---|---|---|
| 1-183 | Al | [4-phenyl-2,6-naphthyl] | [thiophene-2,5-diyl] | 1 | [3-(perdeuteriophenyl)phenyl] |
| 1-184 | Al | [4-phenyl-2,6-naphthyl] | [thiophene-2,5-diyl] | 1 | [3,5-diphenylphenyl] |
| 1-185 | Al | [4-phenyl-2,6-naphthyl] | [thiophene-2,5-diyl] | 1 | [2,6-diphenylphenyl] |
| 1-186 | Al | [4-phenyl-2,6-naphthyl] | [thiophene-2,5-diyl] | 1 | [2-naphthyl] |
| 1-187 | Al | [4-phenyl-2,6-naphthyl] | [thiophene-2,5-diyl] | 1 | [1-naphthyl] |
| 1-188 | Al | [4-phenyl-2,6-naphthyl] | [thiophene-2,5-diyl] | 1 | [1,1'-binaphthyl-5-yl] |
| 1-189 | Al | [4-phenyl-2,6-naphthyl] | [thiophene-2,5-diyl] | 1 | [1,1'-binaphthyl-4-yl] |

TABLE 1-continued
| Formula | M | A | B | l | C |
|---|---|---|---|---|---|
| 1-190 | Al | 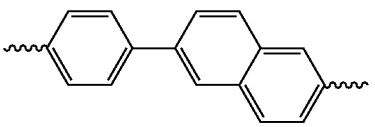 | 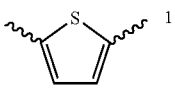 | 1 | 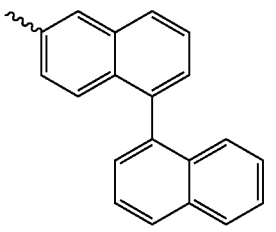 |
| 1-191 | Al | 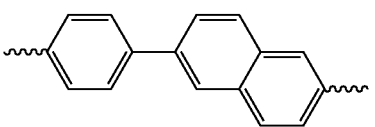 | 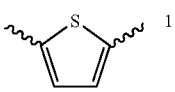 | 1 | 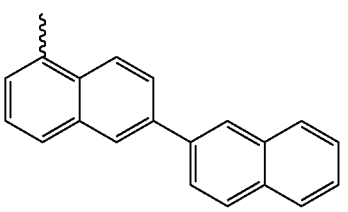 |
| 1-192 | Al | 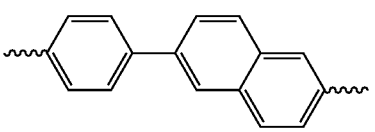 | 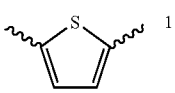 | 1 | 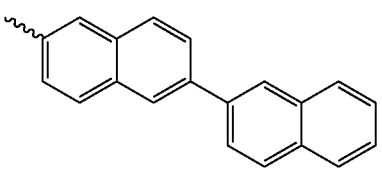 |
| 1-193 | Al | 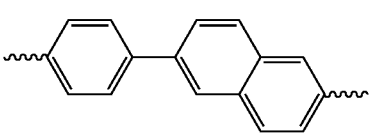 | 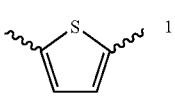 | 1 | 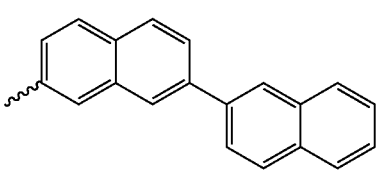 |
| 1-194 | Al | 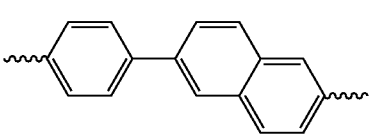 | 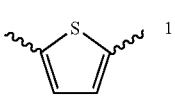 | 1 | 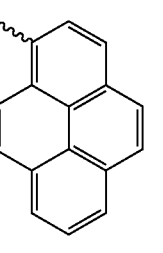 |
| 1-195 | Al | 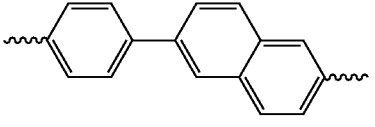 | 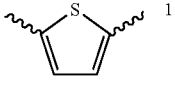 | 1 | 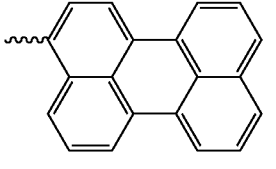 |
| 1-196 | Al | 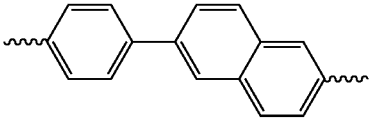 | 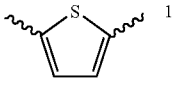 | 1 | 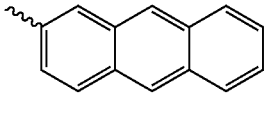 |
| 1-197 | Al | 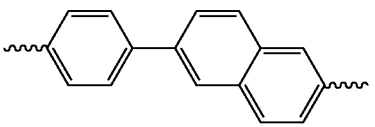 | 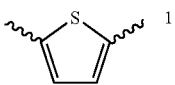 | 1 | 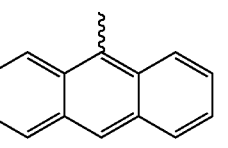 |

TABLE 1-continued
| Formula | M | A | B | l | C |
|---|---|---|---|---|---|
| 1-198 | Al | 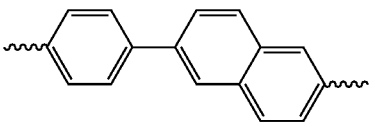 | 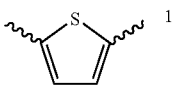 | 1 | 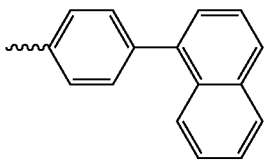 |
| 1-199 | Al | 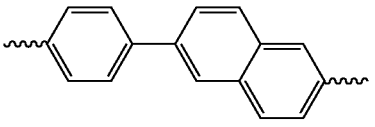 | 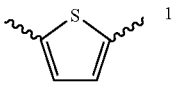 | 1 | 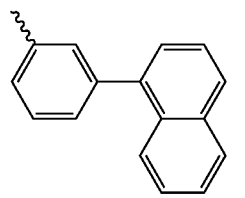 |
| 1-200 | Al | 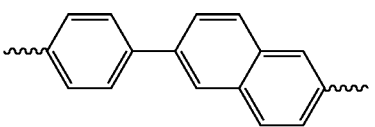 | 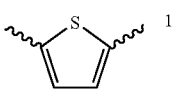 | 1 | 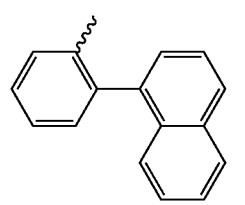 |
| 1-201 | Al | 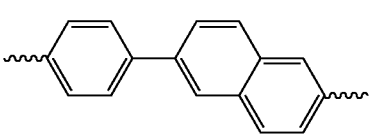 | 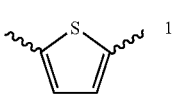 | 1 | 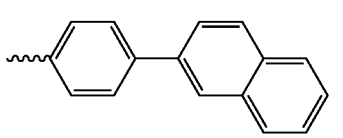 |
| 1-202 | Al | 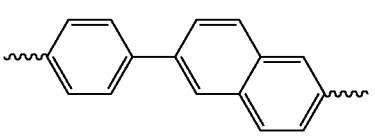 | 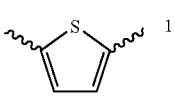 | 1 | 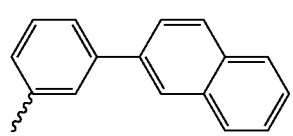 |
| 1-203 | Al | 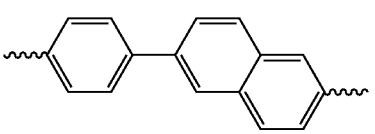 | 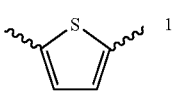 | 1 | 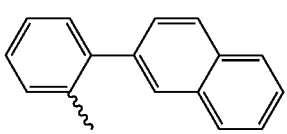 |
| 1-204 | Al | 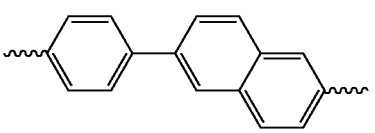 | 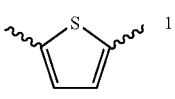 | 1 | 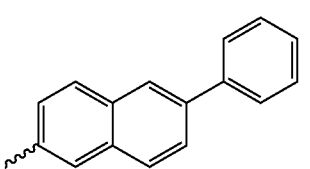 |
| 1-205 | Al | 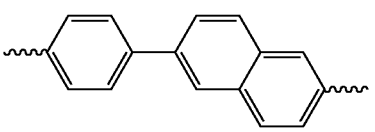 | 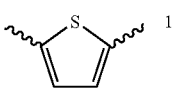 | 1 | 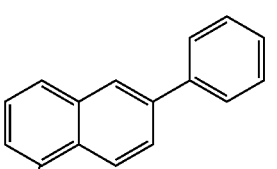 |
| 1-206 | Al | 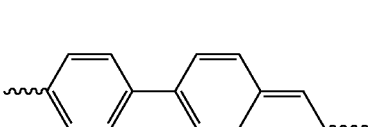 | 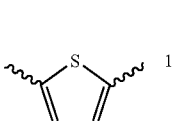 | 1 | 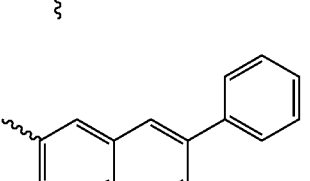 |

TABLE 1-continued

| Formula | M | A | B | l | C |
|---|---|---|---|---|---|
| 1-207 | Al | [phenyl-naphthyl] | [thiophene] | 1 | [naphthyl-phenyl] |
| 1-208 | Al | [phenyl-naphthyl] | [thiophene] | 1 | [phenyl-$CF_3$] |
| 1-209 | Al | [phenyl-naphthyl] | [thiophene] | 1 | [phenyl-CN] |
| 1-210 | Al | [phenyl-naphthyl] | [thiophene] | 1 | [phenyl-($CH_3$)$_2$] |

The organic metal complex derivative represented by Formula 1 of the present invention can be used due to its structural property as an organic material layer in an organic electronic device and organic light emitting device.

The organic metal complex derivative according to the present invention can be applied to the organic light emitting device by a typical preparation method of organic light emitting device.

Figure 2:
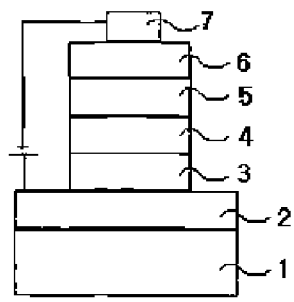
FIGS. 2 to 6 are cross-sectional views illustrating the structure of the organic light emitting device according to the present invention.
Figure 3:
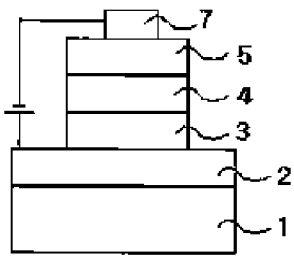
Figure 4:
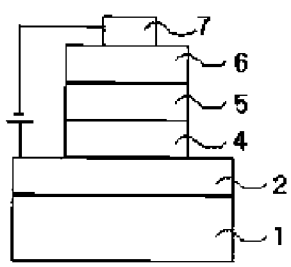
Figure 5:
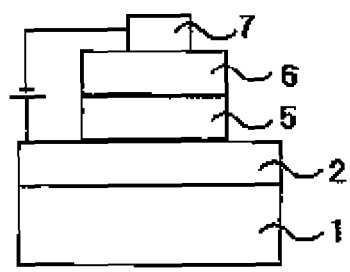
Figure 6:
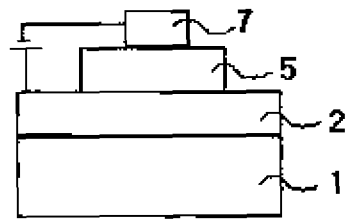

In one embodiment of the present invention, the organic light emitting device has a structure comprising a first electrode, a second electrode, and organic material layers disposed therebetween, and can be prepared by using typical method and materials, except for using the organic metal complex derivative according to the present invention as the organic material layer of organic light emitting device. The structure of the Organic light emitting device according to the present invention is illustrated in FIGS. 2 to 6.

For example, the organic light emitting device according to the present invention can be prepared by depositing a metal, a metal oxide having conductivity, or an alloy thereof on a substrate using a PVD (physical vapor deposition) process such as sputtering and e-beam evaporation to form an anode; forming an organic material layer comprising a hole injecting layer, a hole transporting layer, a light emitting layer, and an electron transporting layer on the anode; and depositing a material, which can be used as a cathode, thereon. Alternatively, the organic light emitting device can be prepared by sequentially depositing a cathode material, an organic material layer, and an anode material on a substrate.

The organic material layer may be of a multilayer structure containing a hole injecting layer, a hole transporting layer, a light emitting layer, an electron transporting layer, and the like, but not limited thereto, or may be of a monolayer structure. Further, the organic material layer can be produced to have a fewer number of layers, by using a variety of polymeric materials, by means of a solvent process rather than a deposit process, such as spin coating, dip coating, doctor blading, screen printing, ink jet printing, and heat transfer processes.

The anode material is preferably a material having a large work function to facilitate hole injection usually to an organic material layer. Specific examples of the anode material which can be used in the present invention include metals such as vanadium, chromium, copper, zinc and gold, or an alloy thereof; metal oxides such as zinc oxide, indium oxide, indium-tin oxide (ITO), and indium zinc oxide (IZO); a combination of a metal and an oxide such as ZnO:Al and $SnO_2$:Sb; conductive polymers such as poly(3-methylthiophene), poly[3,4-(ethylene-1,2-dioxy)thiophene] (PEDT), polypyrrole, and polyaniline, but not limited thereto.

The cathode material is preferably a material having a small work function to facilitate electron injection usually to an organic material layer. Specific examples of the cathode material include metals such as magnesium, calcium, sodium, potassium, titanium, indium, yttrium, lithium, gadolinium, aluminum, silver, tin and lead, or an alloy thereof; multilayer structure materials such as LiF/Al and $LiO_2$/Al, but not limited thereto.

Generally, the following materials can be used for a hole injecting material, a hole transporting material, a light emitting material, and electron transporting material.

The hole injecting material is a material facilitating hole injection from an anode at low voltage. The HOMO (highest occupied molecular orbital) level of the hole injecting material is preferably located between the work function of the anode materials and the HOMO level of its neighboring organic material layer. Specific examples of the hole injecting material include organic materials of metal porphyrin, oligothiophene, and arylamine series, organic materials of hexanitrile hexaazatriphenylene and quinacridone series, organic materials of perylene series, and conductive polymers of anthraquinone, polyaniline, and polythiophene series, but are not limited thereto.

The hole transporting material is preferably a material having high hole mobility, which can transfer holes from the anode or the hole injecting layer toward the light emitting layer. Specific examples thereof include organic materials of arylamine series, conductive polymers, and block copolymers having both conjugated portions and non-conjugated portions, but are not limited thereto.

The light emitting material are a material capable of emitting visible light by accepting and recombining holes from the hole transporting layer and electrons from the electron transporting layer, preferably a material having high quantum efficiency for fluorescence and phosphorescence. Specific examples thereof include 8-hydroxyquinoline aluminum complex ($Alq_3$); compounds of carbazole series; dimerized styryl compounds; BAlq; 10-hydroxybenzoquinoline-metal compounds; compounds of benzoxazole, benzthiazole, and benzimidazole series; polymers of poly(p-phenylenevinylene) (PPV) series; spiro compounds; and compounds of polyfluorene and rubrene series, but are not limited thereto.

The electron transporting material is suitably a material having high electron mobility, which can transfer electrons from the cathode to the light emitting layer. Specific examples thereof include 8-hydroxyquinoline aluminum complex ($Alq_3$); complexes including $Alq_3$; organic radical compounds; and hydroxyflavone-metal complexes, but are not limited thereto.

The organic light emitting device according to the invention may be of a front-side, backside or double-sided light emission according to the materials used.

The compound according to the invention can function in an organic electronic device including an organic solar cell, an organic photoconductor, and an organic transistor, according to a principle similar to that applied to the organic light emitting device.

MODE FOR THE INVENTION

Hereinafter, the present invention will be described in detail in light of Examples. The present invention may, however, be embodied in many different forms and should not be construed as being limited to the Examples set forth herein. Rather, these Examples are provided such that this disclosure will be thorough and complete and will fully convey the concept of the present invention to those skilled in the art.

Preparation Example 1

Synthesis of Ligand 1

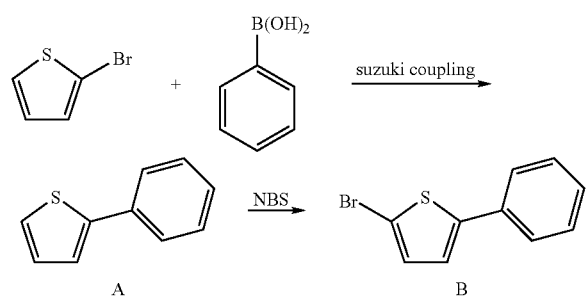

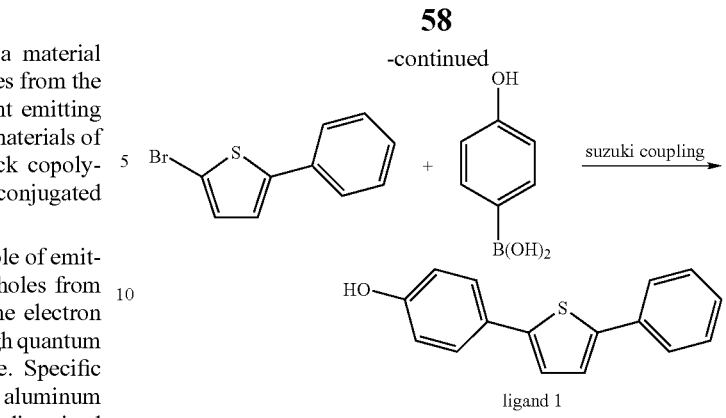

ligand 1

1) Synthesis of Compound A 2-bromothiophene (1.7 g, 10.3 mmol) and phenylboronic acid (1.4 g, 11.4 mmol) were dissolved in tetrahydrofuran (20 mL), and then 2M $K_2CO_3$ (20 mL) was added thereto. Temperature was increased to 50° C., and then tetrabistriphenylphosphinopalladium ($Pd(PPh_3)_4$) (120 ng, 0.1 mmol) was added thereto, and temperature was increased to 65° C., followed by stirring for 4 hrs. Temperature was reduced to room temperature, and then an aqueous layer was removed. An organic layer was dried over magnesium sulfate anhydride to remove residual water, and then filtered to remove magnesium sulfate anhydride. The solvent was completely removed from the organic layer by distillation under reduced pressure, and then hexane was added thereto at room temperature, followed by stirring for 10 min. The produced precipitate was filtered out, and the filtrate was cooled to −10° C., followed by slowly stirring for 1 hr. The produced precipitate was filtered out, and then the filtrate was dried under vacuum at room temperature to give a compound A (1.5 g) with a yield of 94%.

2) Synthesis of Compound B

The compound A (1.5 g, 9.4 mmol) was completely dissolved in chloroform (100 mL), and then N-bromosuccinimide (1.7 g, 9.4 mmol) was slowly added thereto, followed by stirring at room temperature for 30 min. The solvent was completely removed by distillation under reduced pressure, and then ethanol was added thereto at 0° C., followed by stirring for 20 min. The produced precipitate was filtered out, and then the filtrate was dried under vacuum at room temperature to give a compound B (2.2 g) with a yield of 100%.

3) Synthesis of Ligand 1

The compound B (2.2 g, 9.4 mmol) and 4-hydroxyphenylboronic acid (1.3 g, 9.4 mmol) were dissolved in tetrahydrofuran (90 mL), and then 2M $K_2CO_3$ (90 mL) was added thereto. Temperature was increased to 50° C., and then tetrabistriphenylphosphinopalladium ($Pd(PPh_3)_4$) (108 mg, 9.4× $10^{-2}$ mmol) was added thereto, and temperature was increased to 65° C., followed by stirring for 1 hr. Temperature was reduced to room temperature, and then an aqueous layer was removed. An organic layer was dried over magnesium sulfate anhydride to completely remove residual water, and then filtered. The solvent was completely removed from the filtrate by distillation under reduced pressure, and then the resultant was added to chloroform (100 mL), and stirred under heating for 1 hr. Temperature was reduced to room temperature, and filtered, dried to give a ligand 1 (1.8 g) with a yield of 76%.

MS: $[M+H]^+$=252

Preparation Example 2

Synthesis of Ligand 2

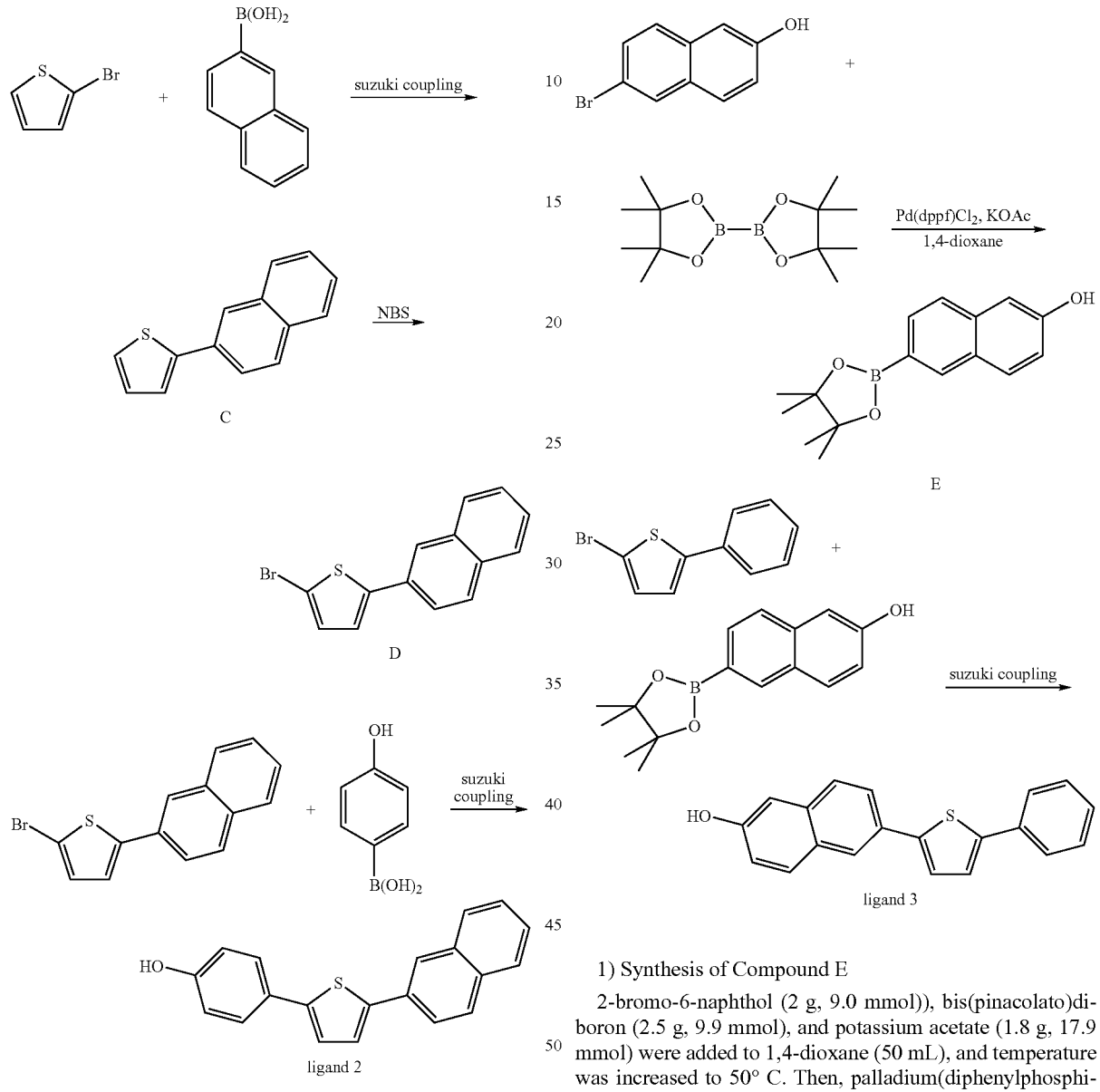

1) Synthesis of Compound C

A compound C was obtained in the same manner as in the preparation method of compound A, except for using 2-naphthylboronic acid instead of phenylboronic acid.

2) Synthesis of Compound D

A compound D was obtained in the same manner as in the preparation method of compound B, except for using the compound C instead of the compound A.

3) Synthesis of Ligand 2

A ligand 2 was obtained in the same manner as in the preparation method of ligand 1, except for using the compound D instead of the compound B.

MS: $[M+H]^+=303$

Preparation Example 3

Synthesis of Ligand 3

1) Synthesis of Compound E 2-bromo-6-naphthol (2 g, 9.0 mmol)), bis(pinacolato)diboron (2.5 g, 9.9 mmol), and potassium acetate (1.8 g, 17.9 mmol) were added to 1,4-dioxane (50 mL), and temperature was increased to 50° C. Then, palladium(diphenylphosphinoferrocene)chloride (73 mg, 9.0×10$^{-2}$ mmol) were added thereto, and the mixture was stirred under heating for 5 hrs. Temperature was reduced to room temperature, and the mixture was diluted with water (50 mL), and extracted with dichloromethane (3×50 mL). An organic extract was dried over magnesium sulfate anhydride, and concentrated under vacuum. The resultant was washed with ethanol, and dried under vacuum to give a compound E (1.2 g) with a yield of 79%.

2) Synthesis of Ligand 3

A ligand 3 was obtained in the same manner as in the preparation method of ligand 1, except for using the compound E instead of the compound B.

MS: $[M+H]^+=303$

Example 1

Synthesis of Formula 1-38

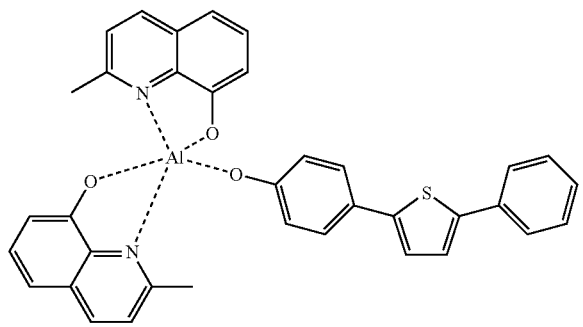

1.9 M triethyl aluminum (1 equivalent) in toluene was added to anhydrous toluene, and then 8-hydroxyquinaldine (2 equivalents) in anhydrous toluene was slowly added thereto. Then, the mixture was stirred under heating until the color became transparent yellow. The ligand 1 (1 equivalent) prepared in Preparation Example 1 was dissolved in anhydrous toluene or anhydrous tetrahydrofuran, and then slowly added thereto, followed by stirring under heating for 1 to 4 hrs. Then, temperature was reduced to room temperature to produce the precipitate. Ethanol was added thereto, and then the precipitate was filtered. The filtered solid was recrystallized using dichloromethane or toluene and ethanol, and then dried under vacuum to obtain an aluminum complex. The aluminum complex represented by Formula 1-38 was analyzed by NMR and MS analysis.

MS: [M–H]$^-$=593, [M–L–H]$^-$=341, [L–H]=251; Tm: 109.4° C., Tg: 247.36° C.

Example 2

Synthesis of Formula 1-46

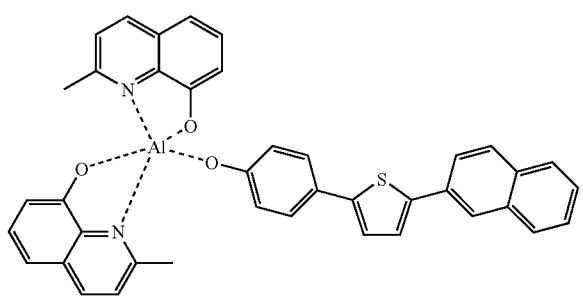

An aluminum complex compound of Formula 1-46 was obtained in the same manners as in Example 1, except for using the ligand 2 prepared in Preparation Example 2 instead of the ligand 1 of Example 1. The aluminum complex represented by Formula 1-46 was analyzed by NMR and MS analysis.

MS: [M–H]$^-$=645, [M–L–H]$^-$=341, [L–H]$^-$=302

Example 3

Synthesis of Formula 1-143

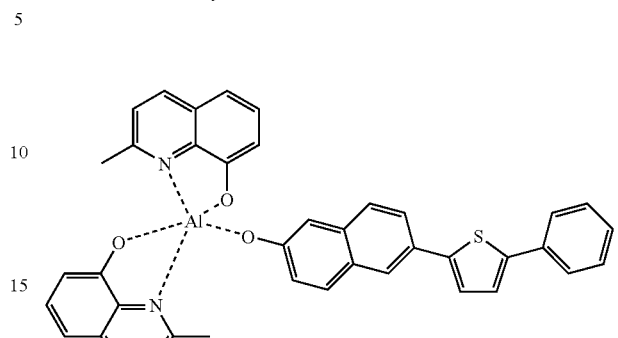

An aluminum complex compound of Formula 1-143 was obtained in the same manners as in Example 1, except for using the ligand 3 prepared in Preparation Example 3 instead of the ligand 1 of Example 1.

MS: [M–H]$^-$=645, [M–L–H]$^-$=341, [L–H]$^-$=302

Experimental Example 1

A glass substrate (Corning 7059 glass) on which a thin film of ITO (indium tin oxide) was coated to a thickness of 1000 Å was immersed in distilled water containing a detergent to wash the substrate with ultrasonic waves. At this time, the detergent was a product commercially available from Fisher Co. and the distilled water has been filtered previously by using a filter commercially available from Millipore Co. ITO was washed for 30 minutes, and then washing with ultrasonic waves was repeated twice for 10 minutes by using distilled water. After the completion of washing with distilled water, washing with ultrasonic waves was carried out by using solvents such as isopropyl alcohol, acetone and methanol.

On the ITO electrode thus prepared, the following hexanitrile hexaazatriphenylene (HAT) (500 Å) was vacuum-deposited to form a hole injecting layer.

[HAT]

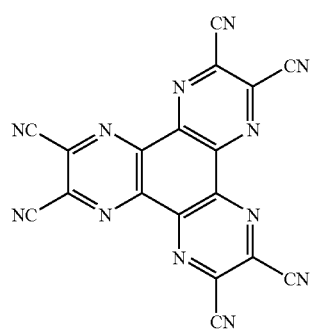

On the hole injecting layer, the following 4,4'-bis[N-(1-naphthyl)-N-phenylamino]biphenyl (NPB) (400 Å) was vacuum-deposited to form a hole transporting layer.

[NPB]

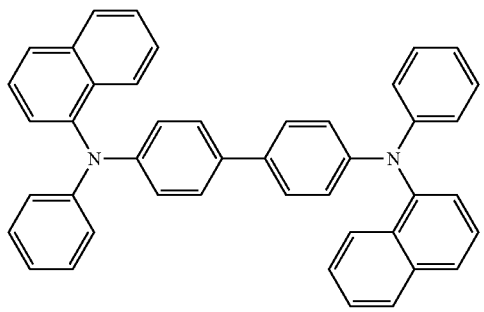 [SMILES: c1ccc(N(c2ccc(-c3ccc(N(c4ccccc4)c4cccc5ccccc45)cc3)cc2)c2cccc3ccccc23)cc1]

On the hole transporting layer, an aluminum complex represented by Formula 1-38 was doped with Btp2Ir(acac) (4%), and vacuum-deposited to form a red light emitting layer.

[Btp2Ir(acac)]

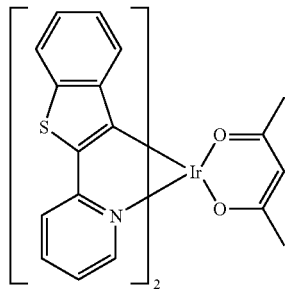

On the red light emitting layer, Alq$_3$ was sequentially vacuum-deposited to a thickness of 200 Å thus to form an electron transporting layer.

[Alq$_3$]

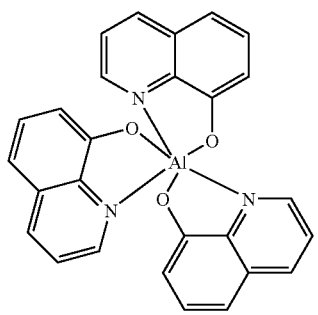

On the electron transporting layer, lithium fluoride (LiF) and aluminum were sequentially vacuum-deposited to a thickness of 12 Å and 2000 Å respectively. A cathode was formed to prepare an organic light emitting device.

In the above process, the deposition rate of the organic material was maintained at 0.4 to 0.7 Å/sec and the deposition rates of lithium fluoride and aluminum of the cathode were maintained at 0.3 Å/sec and 2 Å/sec, respectively. The vacuum degree during deposition was maintained at 2×10$^{-7}$~5×10$^{-8}$ torr.

When a forward electric field of 6.3 V was applied to the organic light emitting device as prepared above, red light emission of 12.1 cd/A was observed with x=0.66, and y=0.34 based on the 1931 CIE color coordinate at a current density of 25 mA/cm$^2$ Comparative Example 1

A glass substrate (Corning 7059 glass) on which a thin film of ITO (indium tin oxide) was coated to a thickness of 1000 Å was immersed in distilled water containing a detergent to wash the substrate with ultrasonic waves. At this time, the detergent was a product commercially available from Fisher Co. and the distilled water has been filtered previously by using a filter commercially available from Millipore Co. ITO was washed for 30 minutes, and then washing with ultrasonic waves was repeated twice for 10 minutes by using distilled water. After the completion of washing with distilled water, washing with ultrasonic waves was carried out by using solvents such as isopropyl alcohol, acetone and methanol.

On the ITO electrode, hexanitrile hexaazatriphenylene (500 Å), and 4,4'-bis[N-(1-naphthyl)-N-phenylamino]biphenyl (NPB) (400 Å), the following BAlq compound doped with 4% Btp2Ir(acac) (300 Å), and Alq$_3$ (200 Å) were sequentially coated by thermal vacuum deposition to form a hole injecting layer, a hole transporting layer, a light emitting layer, and an electron transporting layer, respectively.

[BAlq]

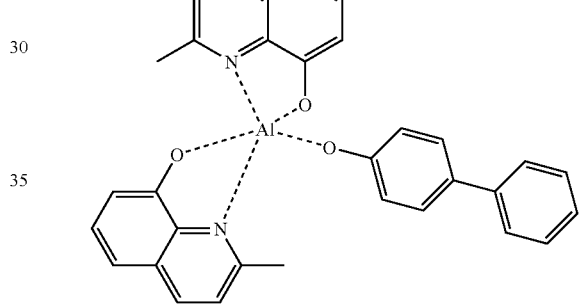

On the electron transporting layer, lithium fluoride (LiF) and aluminum were sequentially vacuum-deposited to a thickness of 12 Å and 2000 Å respectively. A cathode was formed to prepare an organic light emitting device.

In the above process, the deposition rate of the organic material was maintained at 0.4 to 0.7 Å/sec and the deposition rates of lithium fluoride and aluminum of the cathode were maintained at 0.3 Å/sec and 2 Å/sec, respectively. The vacuum degree during deposition was maintained at 2×10$^{-7}$~5×10$^{-8}$ torr.

When a forward electric field of 7.3 V was applied to the organic light emitting device as prepared above, red light emission of 10.7 cd/A was observed with x=0.65, and y=0.34 based on the 1931 CIE color coordinate at a current density of 25 mA/cm$^2$

The invention claimed is:

1. An organic metal complex derivative represented by the following Formula 1:

$$[Y]_n\text{—}M\text{---}L \qquad \text{[Formula 1]}$$

wherein Y is a ligand containing 8-hydroxy-2-methylquinoline, n is 1 to 3,

M is a metal selected from the group consisting of aluminum, zinc, zirconium, iridium, lithium, and molybdenum, L is —O-A-[B]$_l$—C, wherein 1 is 1 to 4, O is oxygen, A is a $C_6$~$C_{40}$ arylene group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group;

B is a compound represented by the following Formula 2,

[Formula 2]

wherein X is any one selected from —O—, —NH—, —S— and —SiRR'—

R and R' are bivalent groups, the same as defined in the following $R_1$ and $R_2$, $R_1$ and $R_2$ are the same as or different from each other, and selected from the group consisting of hydrogen; deuterium; a $C_1$~$C_{40}$ alkyl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; a $C_3$~$C_{40}$ cycloalkyl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; a $C_2$~$C_{40}$ heterocycloalkyl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group, and a $C_5$~$C_{40}$ heteroaryl group; a $C_2$~$C_{40}$ alkenyl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxyl group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; a $C_3$~$C_{40}$ alkoxy group unsubstituted or substituted with one or more groups selected from the group consisting of halogen, deuterium, an amino group, a nitrite group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; an amino group unsubstituted or substituted with one or more groups selected from the group consisting of halogen, deuterium, an amino group, a nitrile group, a nitro group, a $C_1$~$C_{40}$ alkyl group, a heterocycloalkyl group, a $C_6$~$C_{40}$ aryl group and a $C_5$~$C_{40}$ heteroaryl group; a $C_6$~$C_{40}$ aryl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; and a $C_5$~$C_{40}$ heteroaryl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group, and forms an aliphatic, aromatic, heteroaliphatic, or heteroaromatic condensed ring or a spiro bond, together with the adjacent group, and C is selected from the group consisting of deuterium and a $C_6$~$C_{40}$ aryl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group.

2. The organic metal complex derivative according to claim 1, wherein the ligand containing 8-hydroxy-2-methylquinoline is substituted with one or more selected from the group consisting of hydrogen; deuterium; a $C_1$~$C_{40}$ alkyl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; a $C_3$~$C_{40}$ cycloalkyl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; a $C_2$~$C_{40}$ heterocycloalkyl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; a $C_2$~$C_{40}$ alkenyl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; a $C_1$~$C_{40}$ alkoxy group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; an amino group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ hetero cycloalkyl group, a $C_6$~$C_{40}$ aryl group and a $C_5$~$C_{40}$ heteroaryl group; a $C_6$~$C_{40}$ aryl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group; and a $C_5$~$C_{40}$ heteroaryl group unsubstituted or substituted with one or more groups selected from the group consisting of halogen, deuterium, an amino group, a nitrile group, a nitro group, a $C_1$~$C_{40}$ alkyl group, a $C_2$~$C_{40}$ alkenyl group, a $C_1$~$C_{40}$ alkoxy group, a $C_3$~$C_{40}$ cycloalkyl group, a $C_2$~$C_{40}$ heterocycloalkyl group, a $C_6$~$C_{40}$ aryl group and a $C_5$~$C_{40}$ heteroaryl group, or forms an aliphatic, aromatic, heteroaliphatic, or heteroaromatic condensed ring or a spiro bond, together with the adjacent group.

3. The organic metal complex derivative according to claim 1, wherein the organic metal complex derivative represented by Formula 1 is selected from the group consisting of the following Formulae 1-37 to 1-70, 1-72 to 1-105, 1-107 to 1-140, 1-142 to 1-175, and 1-177 to 1-142:

-continued

| Formula | M | A | B | l | C |
|---|---|---|---|---|---|
| 1-45 | Al | phenylene | thienyl | 1 | 2,6-diphenylphenyl |
| 1-46 | Al | phenylene | thienyl | 1 | 2-naphthyl |
| 1-47 | Al | phenylene | thienyl | 1 | 1-naphthyl |
| 1-48 | Al | phenylene | thienyl | 1 | 4-(1-naphthyl)-1-naphthyl |
| 1-49 | Al | phenylene | thienyl | 1 | 4-(1-naphthyl)-1-naphthyl |
| 1-50 | Al | phenylene | thienyl | 1 | 6-(1-naphthyl)-2-naphthyl |
| 1-51 | Al | phenylene | thienyl | 1 | 5-(2-naphthyl)-2-naphthyl |
| 1-52 | Al | phenylene | thienyl | 1 | 6-(2-naphthyl)-2-naphthyl |

-continued
| Formula | M | A | B | 1 | C |
|---|---|---|---|---|---|
| 1-53 | Al | 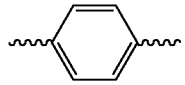 | 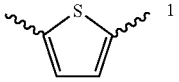 | | 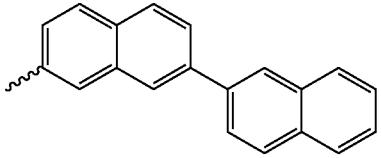 |
| 1-54 | Al | 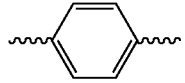 | 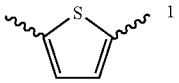 | | 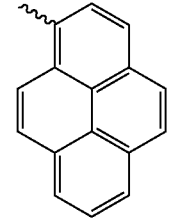 |
| 1-55 | Al | 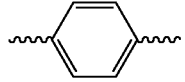 | 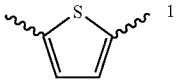 | | 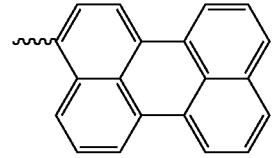 |
| 1-56 | Al | 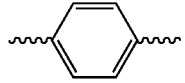 | 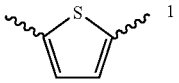 | | 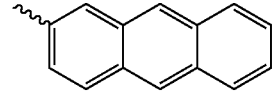 |
| 1-57 | Al | 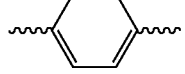 |  | | 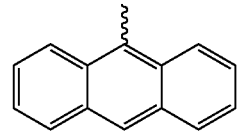 |
| 1-58 | Al |  | 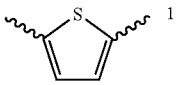 | | 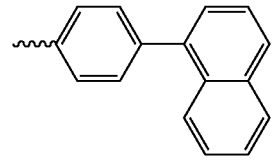 |
| 1-59 | Al |  | 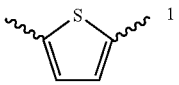 | | 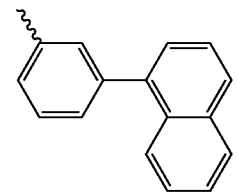 |
| 1-60 | Al |  | 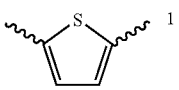 | | 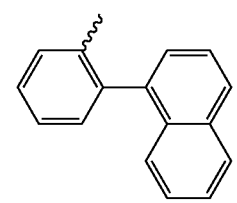 |
| 1-61 | Al |  | 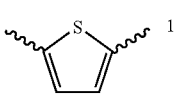 | | 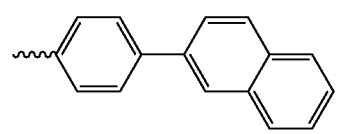 |

-continued

| Formula | M | A | B | 1 | C |
|---|---|---|---|---|---|
| 1-62 | Al | phenylene | thienyl | 1 | 3-(naphthalen-2-yl)phenyl |
| 1-63 | Al | phenylene | thienyl | 1 | 2-(naphthalen-2-yl)phenyl |
| 1-64 | Al | phenylene | thienyl | 1 | 6-phenylnaphthalen-2-yl |
| 1-65 | Al | phenylene | thienyl | 1 | 6-phenylnaphthalen-1-yl |
| 1-66 | Al | phenylene | thienyl | 1 | 7-phenylnaphthalen-2-yl |
| 1-67 | Al | phenylene | thienyl | 1 | 7-phenylnaphthalen-1-yl |
| 1-68 | Al | phenylene | thienyl | 1 | 4-(trifluoromethyl)phenyl |
| 1-69 | Al | phenylene | thienyl | 1 | 3-cyanophenyl |
| 1-70 | Al | phenylene | thienyl | 1 | 3,5-dimethylphenyl |
| 1-72 | Al | phenylene (meta) | thienyl (with D,D) | 1 | D |

-continued
| Formula | M | A | B | l | C |
|---|---|---|---|---|---|
| 1-73 | Al | 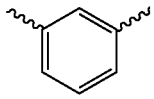 | 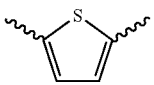 | 1 | 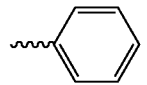 |
| 1-74 | Al | 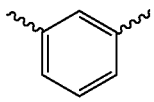 | 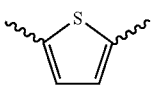 | 1 | 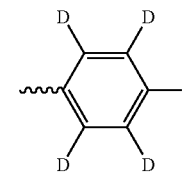 |
| 1-75 | Al | 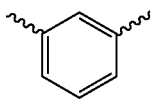 | 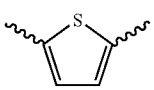 | 1 | 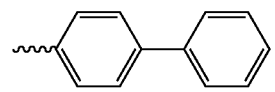 |
| 1-76 | Al | 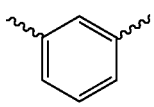 | 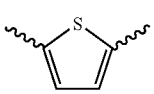 | 1 | 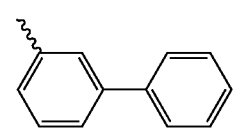 |
| 1-77 | Al | 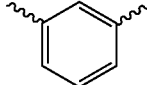 | 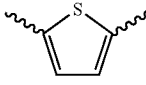 | 1 | 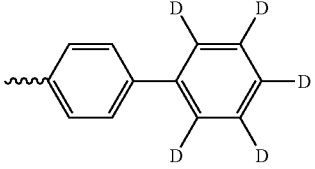 |
| 1-78 | Al | 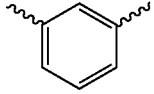 | 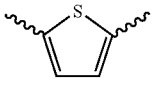 | 1 | 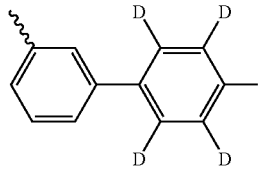 |
| 1-79 | Al | 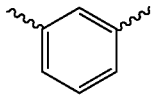 | 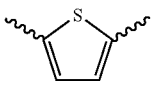 | 1 | 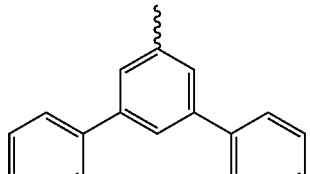 |
| 1-80 | Al |  | 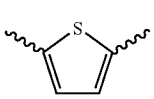 | 1 | 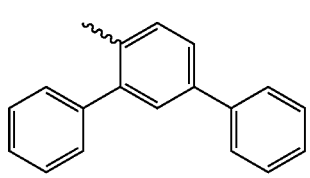 |
| 1-81 | Al | 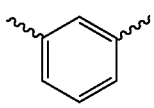 | 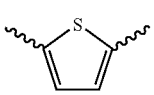 | 1 | 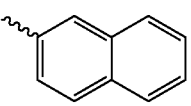 |
| 1-82 | Al |  | 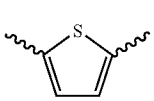 | 1 | 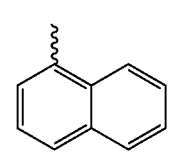 |

-continued
| Formula | M | A | B | l | C |
|---|---|---|---|---|---|
| 1-83 | Al | 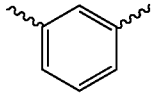 |  | 1 | 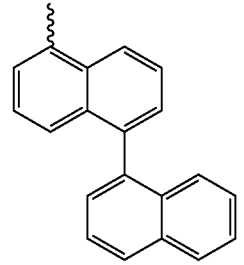 |
| 1-84 | Al | 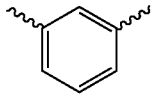 | 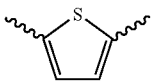 | 1 | 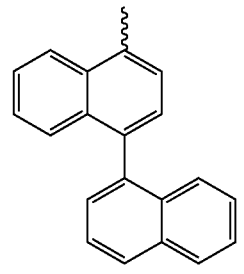 |
| 1-85 | Al | 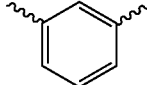 | 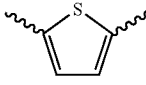 | 1 | 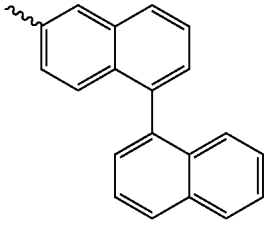 |
| 1-86 | Al | 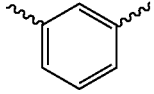 | 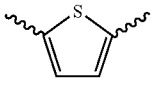 | 1 | 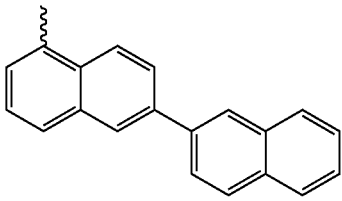 |
| 1-87 | Al | 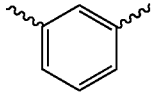 |  | 1 | 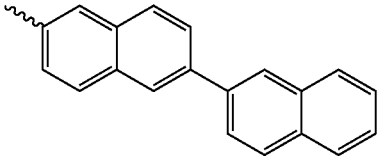 |
| 1-88 | Al | 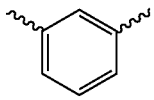 | 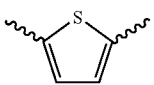 | 1 | 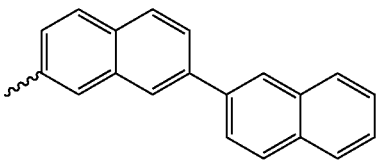 |
| 1-89 | Al | 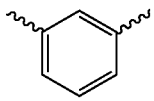 | 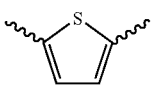 | 1 | 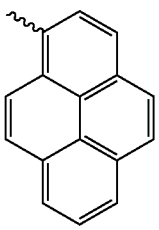 |

-continued
| Formula | M | A | B | 1 | C |
|---|---|---|---|---|---|
| 1-90 | Al | 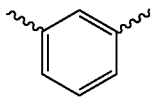 | 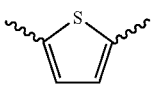 | 1 | 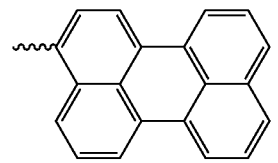 |
| 1-91 | Al | 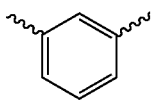 | 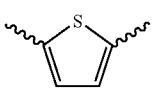 | 1 | 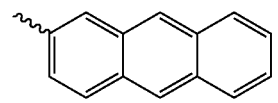 |
| 1-92 | Al | 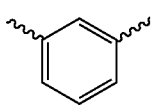 | 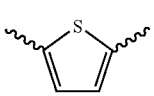 | 1 | 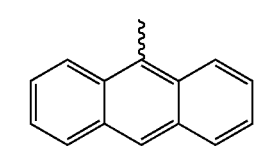 |
| 1-93 | Al | 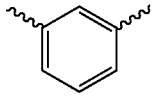 | 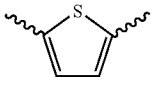 | 1 | 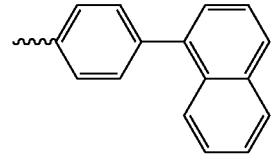 |
| 1-94 | Al | 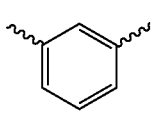 | 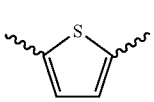 | 1 | 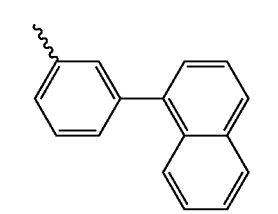 |
| 1-95 | Al | 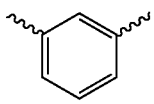 | 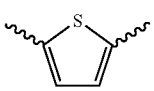 | 1 | 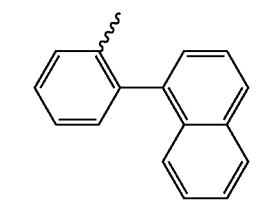 |
| 1-96 | Al | 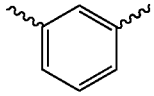 | 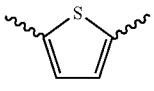 | 1 | 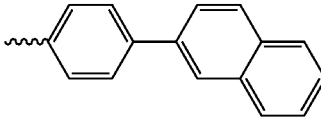 |
| 1-97 | Al | 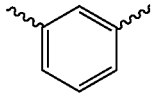 |  | 1 | 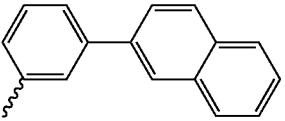 |
| 1-98 | Al | 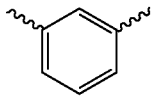 |  | 1 | 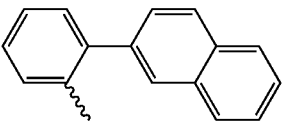 |
| 1-99 | Al | 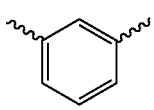 | 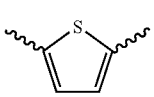 | 1 | 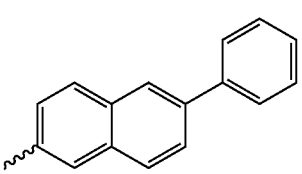 |

-continued
| Formula | M | A | B | 1 | C |
|---|---|---|---|---|---|
| 1-100 | Al | 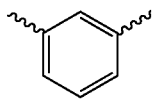 | 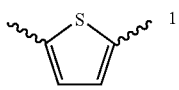 1 | | 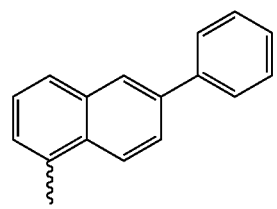 |
| 1-101 | Al | 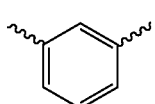 | 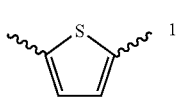 1 | | 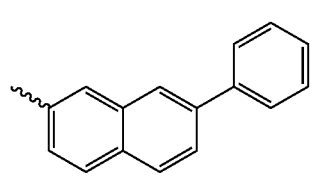 |
| 1-102 | Al | 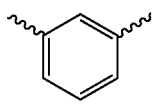 | 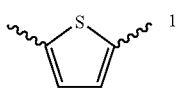 1 | | 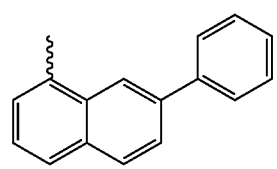 |
| 1-103 | Al | 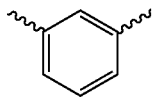 | 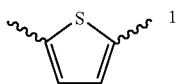 1 | | 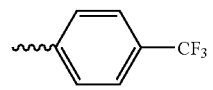 |
| 1-104 | Al |  | 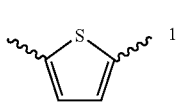 1 | | 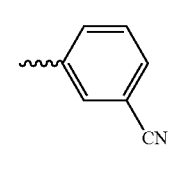 |
| 1-105 | Al | 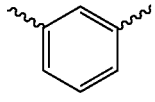 | 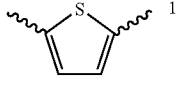 1 | | 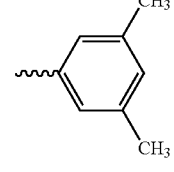 |
| 1-107 | Al | 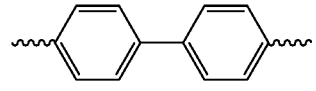 | 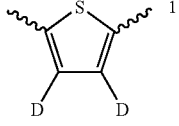 1 | | D |
| 1-108 | Al | 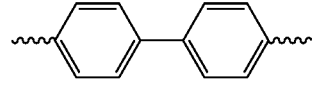 | 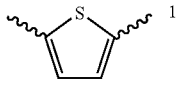 1 | | 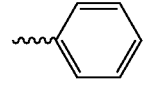 |
| 1-109 | Al | 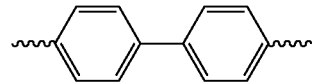 | 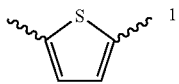 1 | | 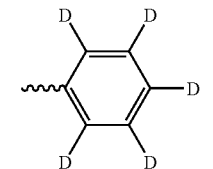 |
| 1-110 | Al | 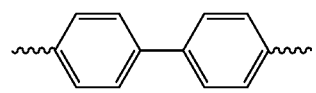 | 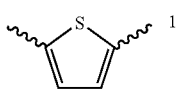 1 | | 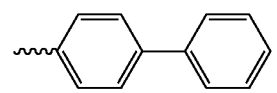 |

-continued

| Formula | M | A | B | | C |
|---|---|---|---|---|---|
| 1-111 | Al | biphenyl-4,4'-diyl | thiophene-2,5-diyl | 1 | biphenyl-3-yl |
| 1-112 | Al | biphenyl-4,4'-diyl | thiophene-2,5-diyl | 1 | 4-(2,3,4,5,6-D$_5$-phenyl)phenyl |
| 1-113 | Al | biphenyl-4,4'-diyl | thiophene-2,5-diyl | 1 | 4-(2,3,4,5,6-D$_5$-phenyl)phenyl |
| 1-114 | Al | biphenyl-4,4'-diyl | thiophene-2,5-diyl | 1 | 3,5-diphenylphenyl |
| 1-115 | Al | biphenyl-4,4'-diyl | thiophene-2,5-diyl | 1 | 2,6-diphenylphenyl |
| 1-116 | Al | biphenyl-4,4'-diyl | thiophene-2,5-diyl | 1 | naphthalen-2-yl |
| 1-117 | Al | biphenyl-4,4'-diyl | thiophene-2,5-diyl | 1 | naphthalen-1-yl |
| 1-118 | Al | biphenyl-4,4'-diyl | thiophene-2,5-diyl | 1 | 1,1'-binaphthalen-5-yl |

-continued

| Formula | M | A | B | l | C |
|---|---|---|---|---|---|
| 1-119 | Al | biphenyl-4,4'-diyl | thiophene-2,5-diyl | 1 | 1,1'-binaphthalen-4-yl |
| 1-120 | Al | biphenyl-4,4'-diyl | thiophene-2,5-diyl | 1 | 1,1'-binaphthalen-5-yl |
| 1-121 | Al | biphenyl-4,4'-diyl | thiophene-2,5-diyl | 1 | 2,2'-binaphthalen-5-yl |
| 1-122 | Al | biphenyl-4,4'-diyl | thiophene-2,5-diyl | 1 | 2,2'-binaphthalen-6-yl |
| 1-123 | Al | biphenyl-4,4'-diyl | thiophene-2,5-diyl | 1 | 2,2'-binaphthalen-7-yl |
| 1-124 | Al | biphenyl-4,4'-diyl | thiophene-2,5-diyl | 1 | pyren-1-yl |
| 1-125 | Al | biphenyl-4,4'-diyl | thiophene-2,5-diyl | 1 | perylen-3-yl |
| 1-126 | Al | biphenyl-4,4'-diyl | thiophene-2,5-diyl | 1 | anthracen-2-yl |

-continued

| Formula | M | A | B | 1 | C |
|---|---|---|---|---|---|
| 1-127 | Al | biphenyl-4,4'-diyl | thiophene-2,5-diyl | 1 | anthracen-9-yl |
| 1-128 | Al | biphenyl-4,4'-diyl | thiophene-2,5-diyl | 1 | 4-(naphthalen-1-yl)phenyl |
| 1-129 | Al | biphenyl-4,4'-diyl | thiophene-2,5-diyl | 1 | 3-(naphthalen-1-yl)phenyl |
| 1-130 | Al | biphenyl-4,4'-diyl | thiophene-2,5-diyl | 1 | 2-(naphthalen-1-yl)phenyl |
| 1-131 | Al | biphenyl-4,4'-diyl | thiophene-2,5-diyl | 1 | 4-(naphthalen-2-yl)phenyl |
| 1-132 | Al | biphenyl-4,4'-diyl | thiophene-2,5-diyl | 1 | 3-(naphthalen-2-yl)phenyl |
| 1-133 | Al | biphenyl-4,4'-diyl | thiophene-2,5-diyl | 1 | 2-(naphthalen-2-yl)phenyl |
| 1-134 | Al | biphenyl-4,4'-diyl | thiophene-2,5-diyl | 1 | 6-phenylnaphthalen-2-yl |
| 1-135 | Al | biphenyl-4,4'-diyl | thiophene-2,5-diyl | 1 | 6-phenylnaphthalen-1-yl |

-continued

| Formula | M | A | B | | C |
|---|---|---|---|---|---|
| 1-136 | Al | biphenyl-4,4'-diyl | thiophene-2,5-diyl | 1 | 6-phenylnaphthalen-2-yl |
| 1-137 | Al | biphenyl-4,4'-diyl | thiophene-2,5-diyl | 1 | 7-phenylnaphthalen-1-yl |
| 1-138 | Al | biphenyl-4,4'-diyl | thiophene-2,5-diyl | 1 | 4-(trifluoromethyl)phenyl (—CF₃) |
| 1-139 | Al | biphenyl-4,4'-diyl | thiophene-2,5-diyl | 1 | 3-cyanophenyl (—CN) |
| 1-140 | Al | biphenyl-4,4'-diyl | thiophene-2,5-diyl | 1 | 3,5-dimethylphenyl (CH₃, CH₃) |
| 1-142 | Al | naphthalene-2,6-diyl | thiophene-2,5-diyl (3,4-D₂) | 1 | D |
| 1-143 | Al | naphthalene-2,6-diyl | thiophene-2,5-diyl | 1 | phenyl |
| 1-144 | Al | naphthalene-2,6-diyl | thiophene-2,5-diyl | 1 | phenyl-d₅ |
| 1-145 | Al | naphthalene-2,6-diyl | thiophene-2,5-diyl | 1 | biphenyl-4-yl |
| 1-146 | Al | naphthalene-2,6-diyl | thiophene-2,5-diyl | 1 | biphenyl-3-yl |

-continued
| Formula | M | A | B | l | C |
|---|---|---|---|---|---|
| 1-147 | Al | 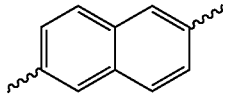 | 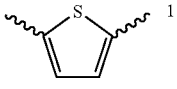 | 1 | 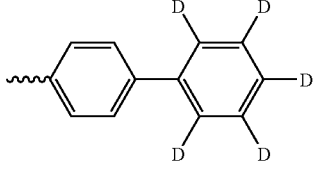 |
| 1-148 | Al | 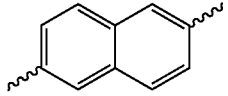 | 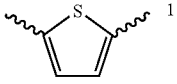 | 1 | 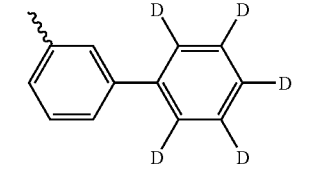 |
| 1-149 | Al | 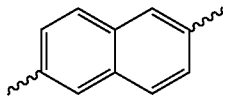 | 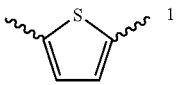 | 1 | 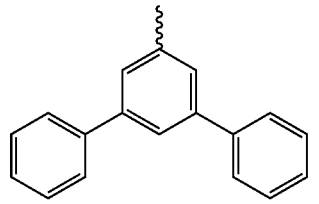 |
| 1-150 | Al | 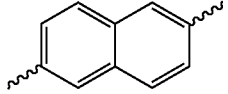 | 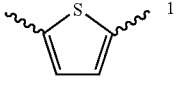 | 1 | 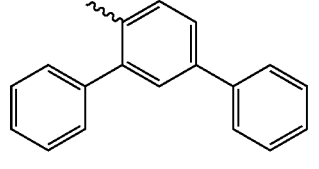 |
| 1-151 | Al | 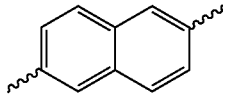 | 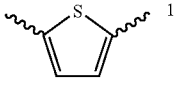 | 1 | 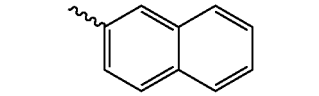 |
| 1-152 | Al | 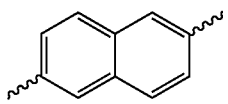 | 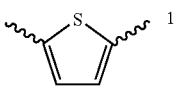 | 1 | 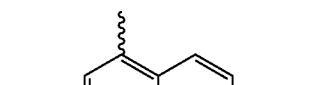 |
| 1-153 | Al | 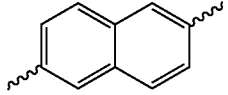 | 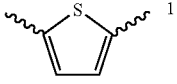 | 1 | 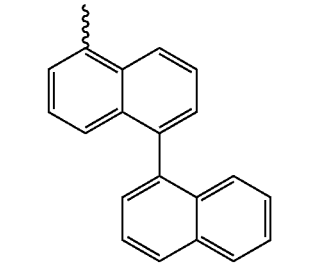 |
| 1-154 | Al | 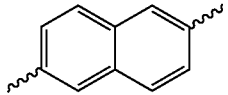 |  | 1 | 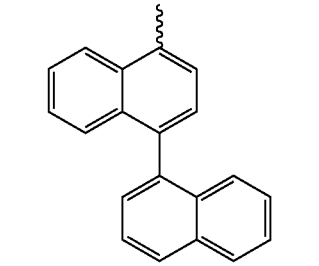 |

-continued
| Formula | M | A | B | l | C |
|---|---|---|---|---|---|
| 1-155 | Al | 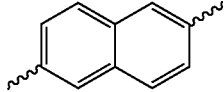 | 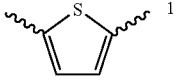 | 1 | 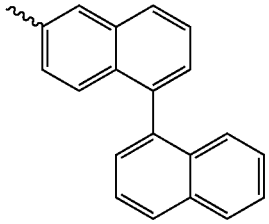 |
| 1-156 | Al | 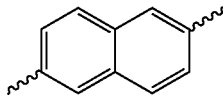 | 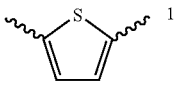 | 1 | 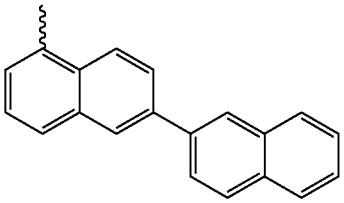 |
| 1-157 | Al | 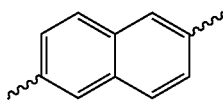 | 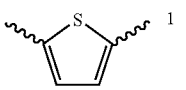 | 1 | 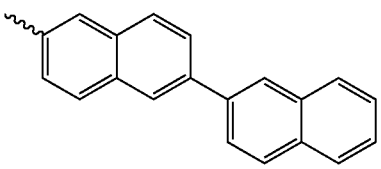 |
| 1-158 | Al | 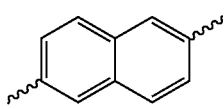 | 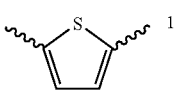 | 1 | 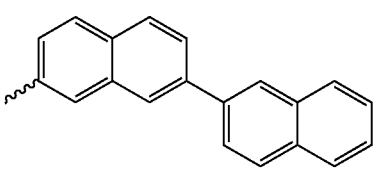 |
| 1-159 | Al | 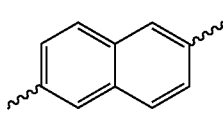 | 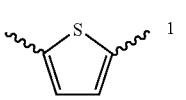 | 1 | 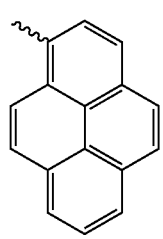 |
| 1-160 | Al | 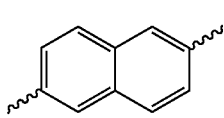 | 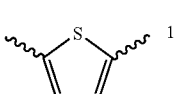 | 1 | 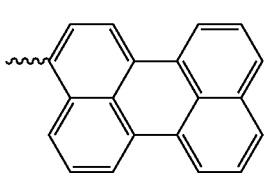 |
| 1-161 | Al | 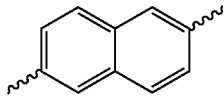 | 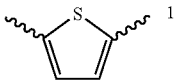 | 1 | 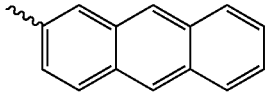 |
| 1-162 | Al | 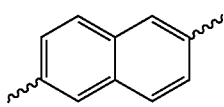 | 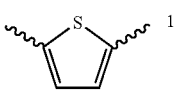 | 1 | 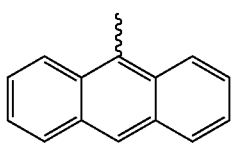 |

-continued
| Formula | M | A | B | l | C |
|---|---|---|---|---|---|
| 1-163 | Al | 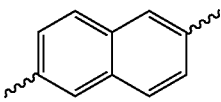 | 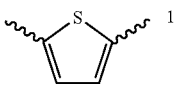 | 1 | 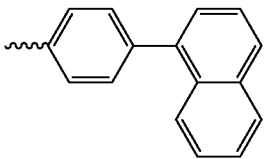 |
| 1-164 | Al | 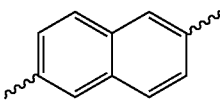 | 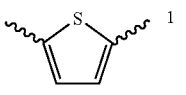 | 1 | 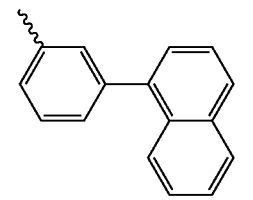 |
| 1-165 | Al | 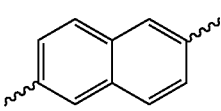 | 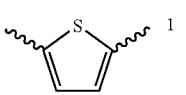 | 1 | 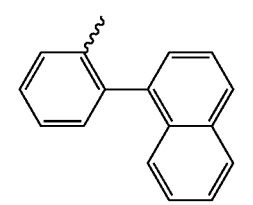 |
| 1-166 | Al | 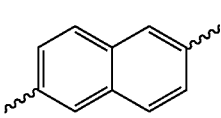 | 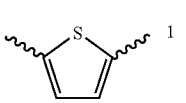 | 1 | 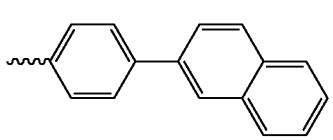 |
| 1-167 | Al | 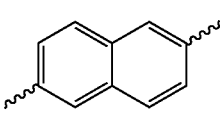 | 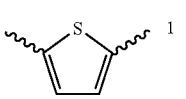 | 1 | 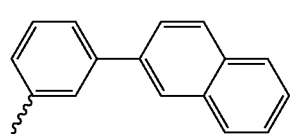 |
| 1-168 | Al | 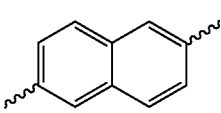 | 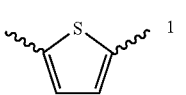 | 1 | 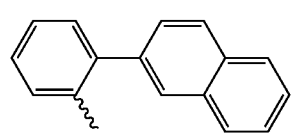 |
| 1-169 | Al | 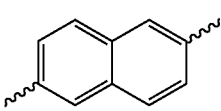 | 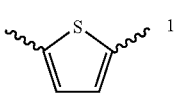 | 1 | 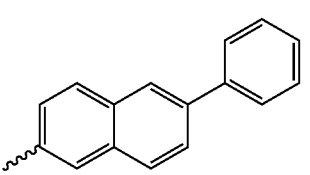 |
| 1-170 | Al | 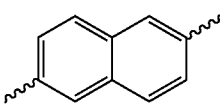 | 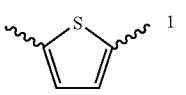 | 1 | 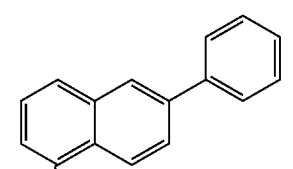 |
| 1-171 | Al | 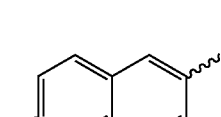 | 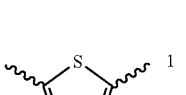 | 1 | 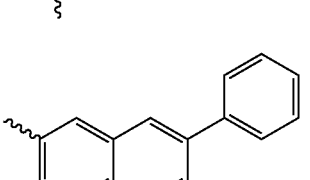 |

-continued

| Formula | M | A | B | | C |
|---|---|---|---|---|---|
| 1-172 | Al | naphthalene-2,6-diyl | thiophene-2,5-diyl | 1 | 2-phenylnaphthalen-8-yl |
| 1-173 | Al | naphthalene-2,6-diyl | thiophene-2,5-diyl | 1 | 4-(CF₃)phenyl |
| 1-174 | Al | naphthalene-2,6-diyl | thiophene-2,5-diyl | 1 | 3-cyanophenyl |
| 1-175 | Al | naphthalene-2,6-diyl | thiophene-2,5-diyl | 1 | 3,5-dimethylphenyl |
| 1-177 | Al | 4-phenyl-naphthalene-2,6-diyl | 3,4-D-thiophene-2,5-diyl | 1 | D |
| 1-178 | Al | 4-phenyl-naphthalene-2,6-diyl | thiophene-2,5-diyl | 1 | phenyl |
| 1-179 | Al | 4-phenyl-naphthalene-2,6-diyl | thiophene-2,5-diyl | 1 | pentadeutero-phenyl |
| 1-180 | Al | 4-phenyl-naphthalene-2,6-diyl | thiophene-2,5-diyl | 1 | biphenyl-4-yl |
| 1-181 | Al | 4-phenyl-naphthalene-2,6-diyl | thiophene-2,5-diyl | 1 | biphenyl-3-yl |
| 1-182 | Al | 4-phenyl-naphthalene-2,6-diyl | thiophene-2,5-diyl | 1 | 4-(pentadeutero-phenyl)phenyl |

-continued
| Formula | M | A | B | l | C |
|---|---|---|---|---|---|
| 1-183 | Al | 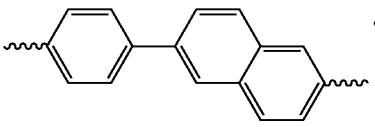 |  | 1 | 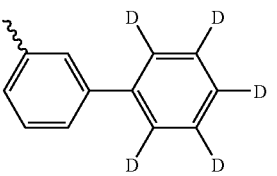 |
| 1-184 | Al | 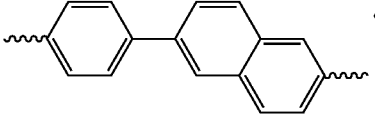 |  | 1 | 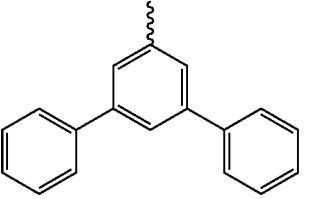 |
| 1-185 | Al | 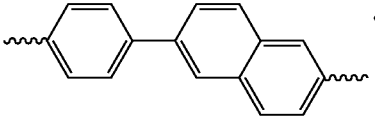 |  | 1 | 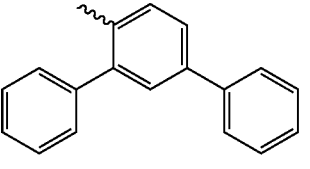 |
| 1-186 | Al | 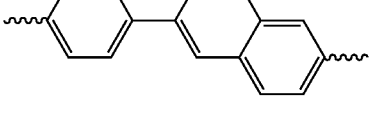 |  | 1 | 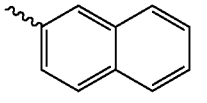 |
| 1-187 | Al | 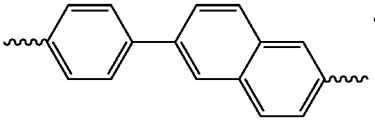 |  | 1 | 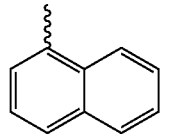 |
| 1-188 | Al | 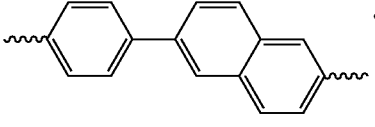 |  | 1 | 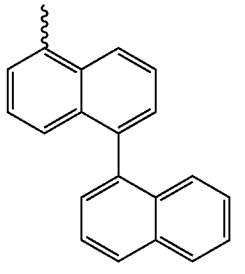 |
| 1-189 | Al | 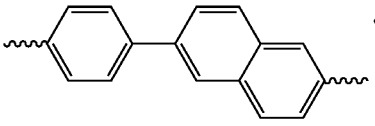 |  | 1 | 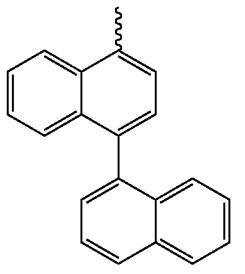 |

-continued
| Formula | M | A | B | 1 | C |
|---|---|---|---|---|---|
| 1-190 | Al | 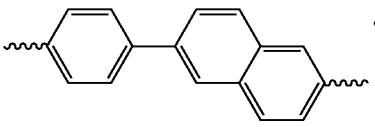 | 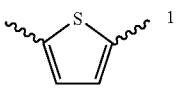 | | 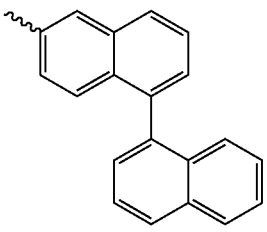 |
| 1-191 | Al | 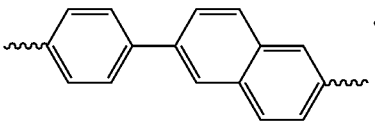 | 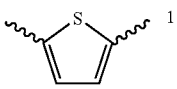 | | 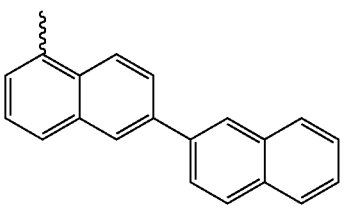 |
| 1-192 | Al | 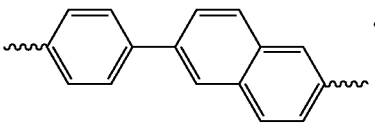 | 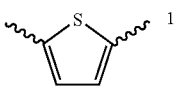 | | 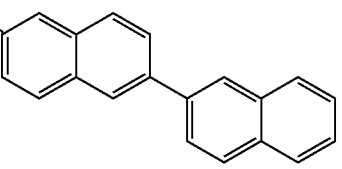 |
| 1-193 | Al | 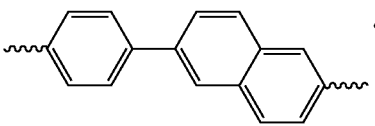 | 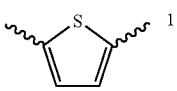 | | 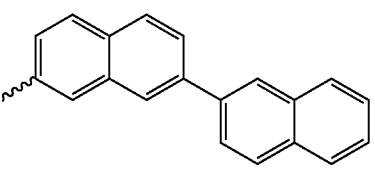 |
| 1-194 | Al | 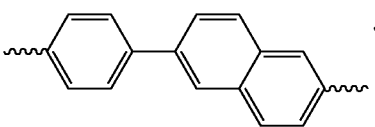 | 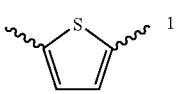 | | 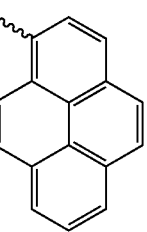 |
| 1-195 | Al | 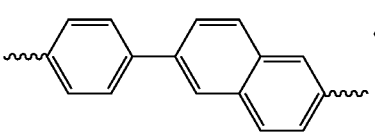 | 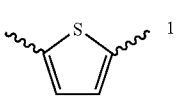 | | 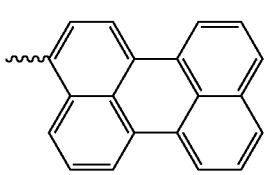 |
| 1-196 | Al | 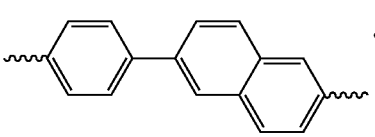 | 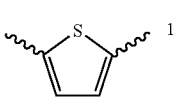 | | 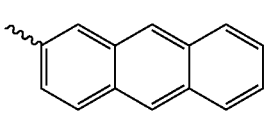 |
| 1-197 | Al | 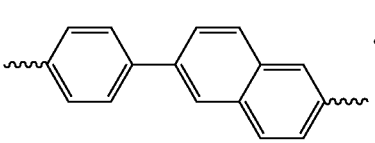 | 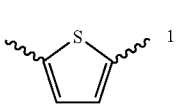 | | 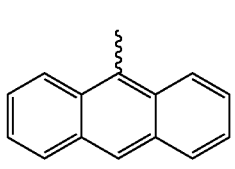 |

-continued
| Formula | M | A | B | l | C |
|---|---|---|---|---|---|
| 1-198 | Al | 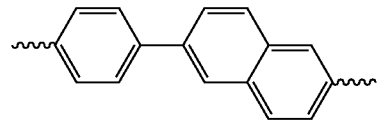 | 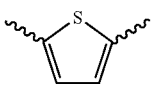 | 1 | 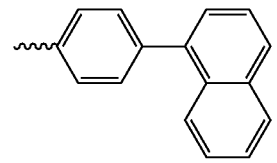 |
| 1-199 | Al | 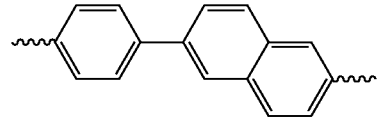 | 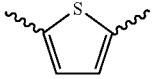 | 1 | 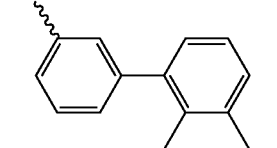 |
| 1-200 | Al | 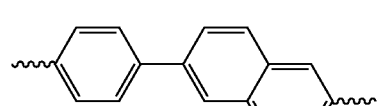 | 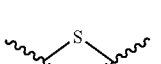 | 1 | 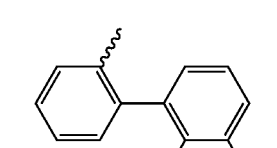 |
| 1-201 | Al | 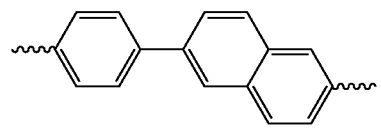 | 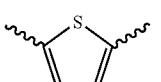 | 1 | 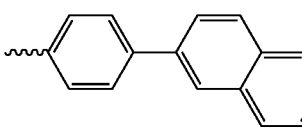 |
| 1-202 | Al | 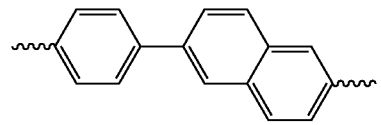 | 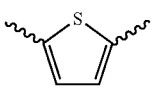 | 1 | 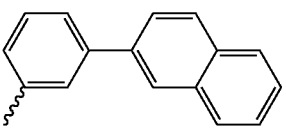 |
| 1-203 | Al | 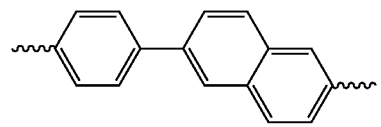 | 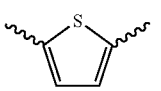 | 1 | 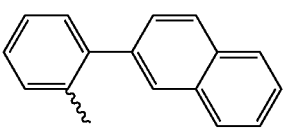 |
| 1-204 | Al | 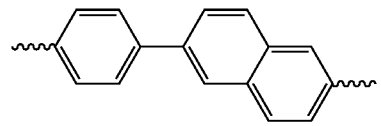 | 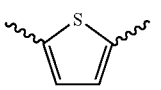 | 1 | 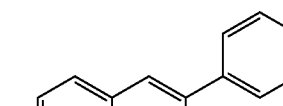 |
| 1-205 | Al | 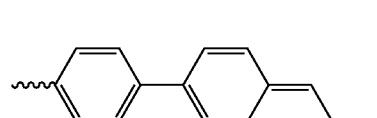 | 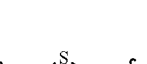 | 1 | 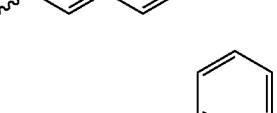 |
| 1-206 | Al | 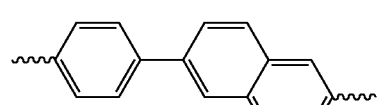 | 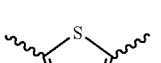 | 1 | 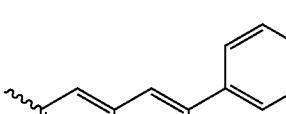 |

-continued

| Formula | M | A | B | l | C |
|---|---|---|---|---|---|
| 1-207 | Al | 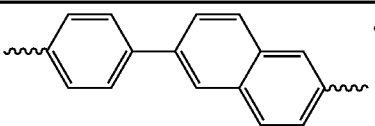 | 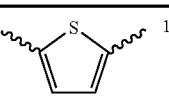 | 1 | 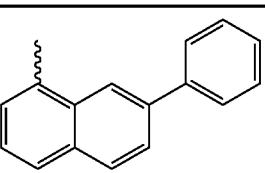 |
| 1-208 | Al | 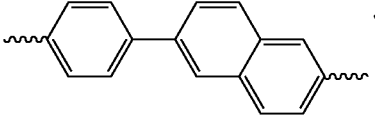 | 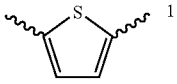 | 1 | 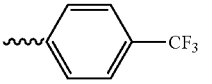 |
| 1-209 | Al | 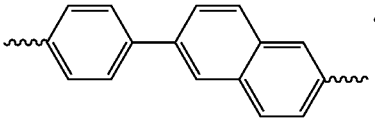 | 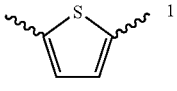 | 1 | 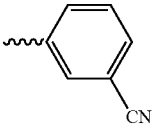 |
| 1-210 | Al | 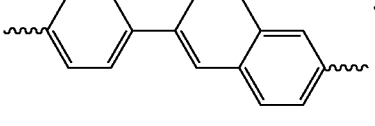 | 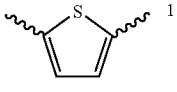 | 1 | 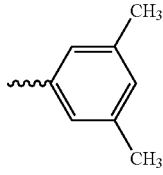 |

4. An organic electronic device comprising a first electrode, a second electrode, and one or more organic material layers disposed therebetween, wherein at least one layer of the organic material layers comprises the organic metal complex derivative of claim 1.

5. The organic electronic device according to claim 4, wherein the organic electronic device is selected from the group consisting of an organic photovoltaic cell, an organic photoconductor (OPC), and an organic transistor.

6. The organic electronic device according to claim 4, wherein at least one layer of the organic material layers contains a light emitting layer, and the light emitting layer includes the organic metal complex derivative.

7. An organic light emitting device having a forward structure which is prepared by sequentially depositing an anode, one or more organic material layers, and a cathode on a substrate, or having a reverse structure which is prepared by sequentially depositing a cathode, one or more organic material layers, and an anode on a substrate, wherein at least one layer of the organic material layers comprises the organic metal complex derivative of claim 1.

8. The organic light emitting device according to claim 7, wherein at least one layer of the organic material layers contains a light emitting layer, and the light emitting layer includes the organic metal complex derivative.

* * * * *